(12) United States Patent
Dalton et al.

(10) Patent No.: US 6,969,480 B2
(45) Date of Patent: *Nov. 29, 2005

(54) METHOD OF PRODUCING STRUCTURES USING CENTRIFUGAL FORCES

(75) Inventors: Paul D. Dalton, Dusseldorf (DE);
Molly S. Shoichet, Toronto (CA);
Stephane G. Levesque, Toronto (CA)

(73) Assignee: matRegen Corp., Toronto (CA)

( * ) Notice: Subject to any disclaimer, the term of this patent is extended or adjusted under 35 U.S.C. 154(b) by 220 days.

This patent is subject to a terminal disclaimer.

(21) Appl. No.: 10/365,532

(22) Filed: Feb. 13, 2003

(65) Prior Publication Data

US 2004/0005423 A1 Jan. 8, 2004

Related U.S. Application Data

(63) Continuation-in-part of application No. 10/169,948, filed as application No. PCT/CA01/00680 on May 11, 2001, now Pat. No. 6,787,090.
(60) Provisional application No. 60/203,910, filed on May 12, 2000.

(51) Int. Cl.[7] .............................................. B29C 39/08
(52) U.S. Cl. ....................... 264/255; 264/267; 264/310; 264/311; 264/349
(58) Field of Search ................................ 264/255, 267, 264/310, 311, 349

(56) References Cited

U.S. PATENT DOCUMENTS

| 3,870,775 | A | * | 3/1975 | Castro et al. ................. 264/53 |
|---|---|---|---|---|
| 5,250,240 | A | | 10/1993 | Kim et al. |
| 5,266,325 | A | | 11/1993 | Kuzma et al. |
| 5,292,515 | A | | 3/1994 | Moro |
| 5,868,976 | A | | 2/1999 | Puglia et al. |
| 6,090,486 | A | * | 7/2000 | Riffle et al. ................. 428/373 |
| 6,589,470 | B2 | * | 7/2003 | Fried et al. ................. 264/443 |

FOREIGN PATENT DOCUMENTS

| DE | 1514410 | 10/1969 |
|---|---|---|
| GB | 2003108 | 3/1979 |
| JP | 63075645 | 3/1988 |
| JP | 04348117 | 12/1992 |

* cited by examiner

Primary Examiner—Stefan Staicovici
(74) Attorney, Agent, or Firm—Lynn C. Schumacher; Hill & Schumacher

(57) ABSTRACT

A variety of hollow structures with unique morphologies were manufactured with a rotational spinning technique. Phase separation of soluble solutions or emulsions was induced within a filled mold as it was being rotated about one of its axis. The density difference between phases results in sediment at the inner lumen of the mold under centrifugal forces. After or during sedimentation, gelation of the phase-separated particles fixes the hollow structure morphology and the solvent remains in the center of the mold. The solvent is removed from the mold resulting in a coating or tube. By controlling the rotational speed and the formulation chemistry, the tube dimensions and wall morphology can be manipulated. This technique offers a new approach to the manufacture of polymeric tubes. It requires small quantities of starting material, permits multi-layering of tubes, is applicable to diverse polymers and can result in highly diffusive hollow structures while maintaining good mechanical strength.

40 Claims, 35 Drawing Sheets

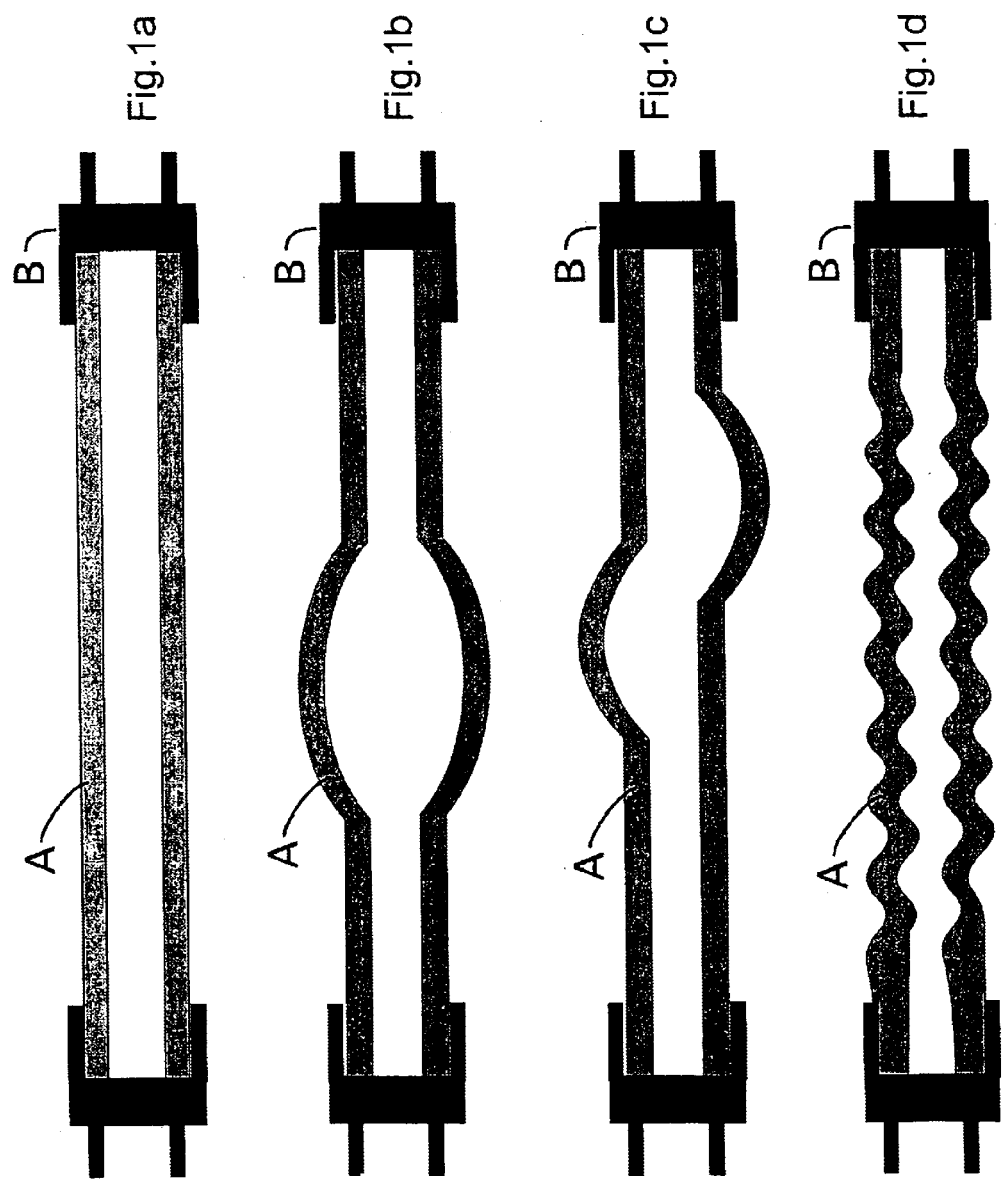

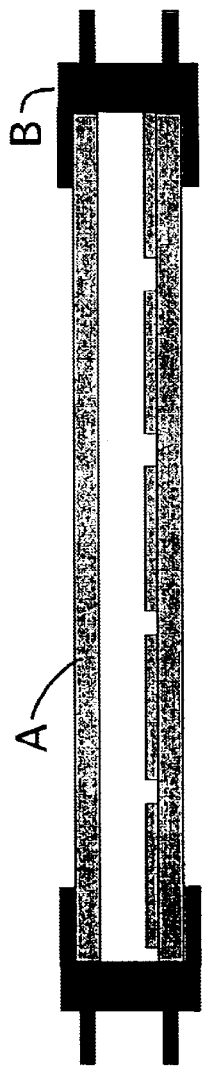
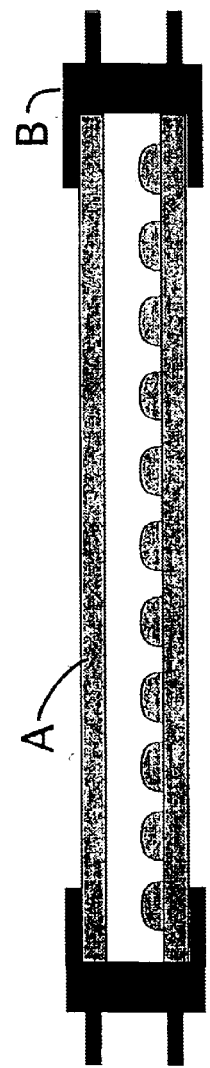
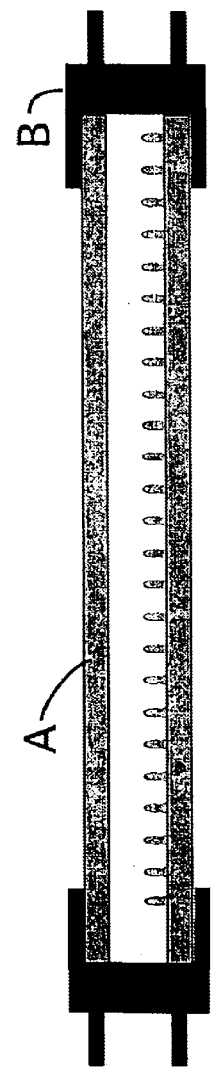
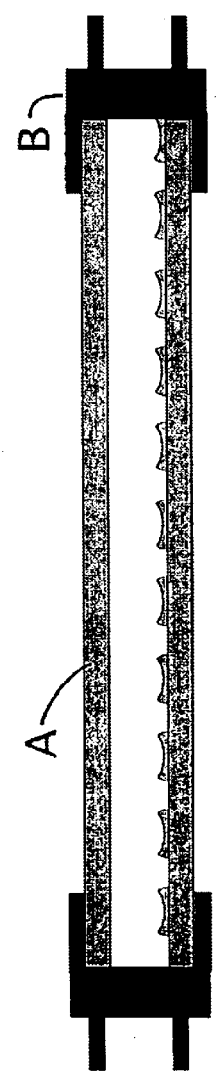

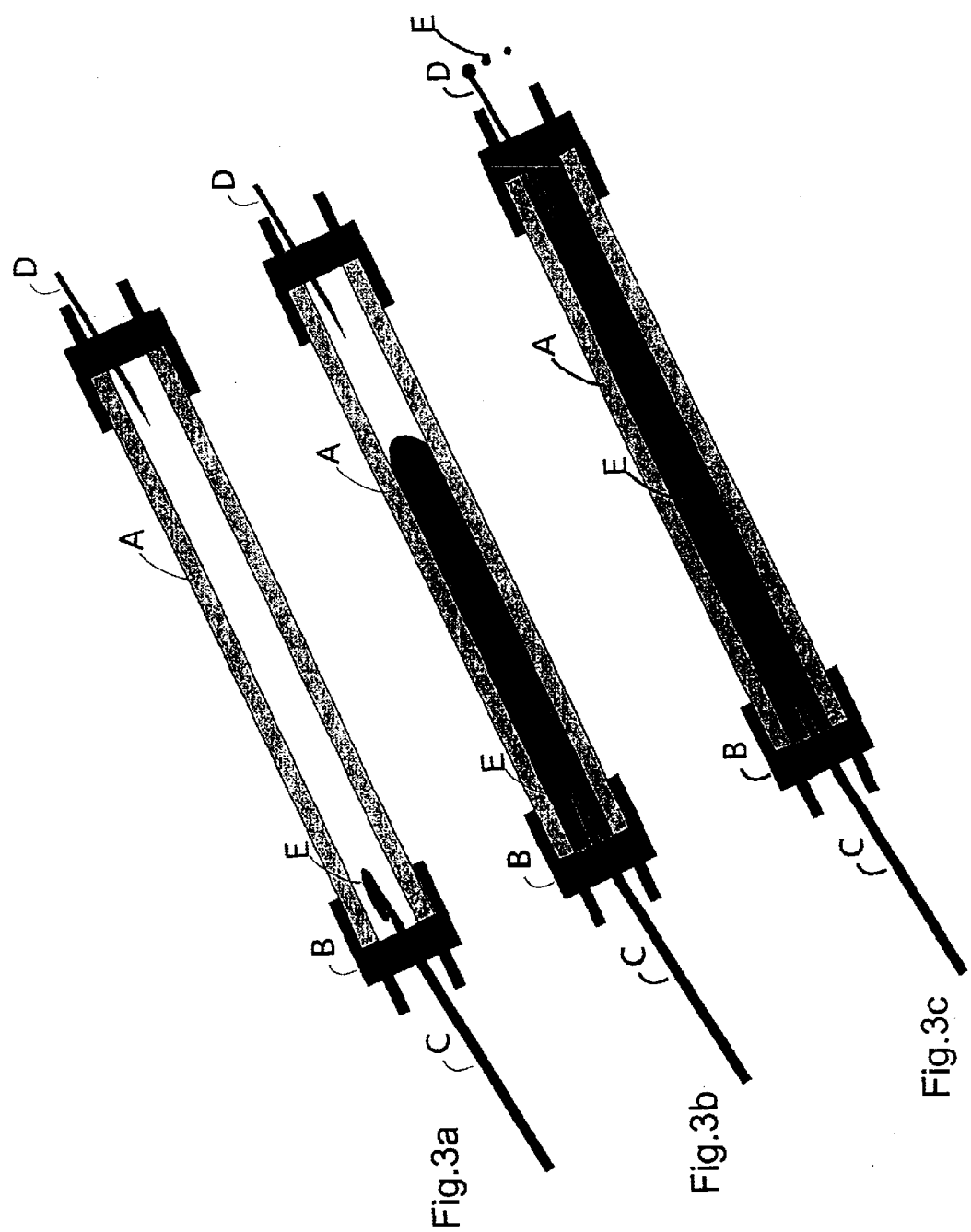

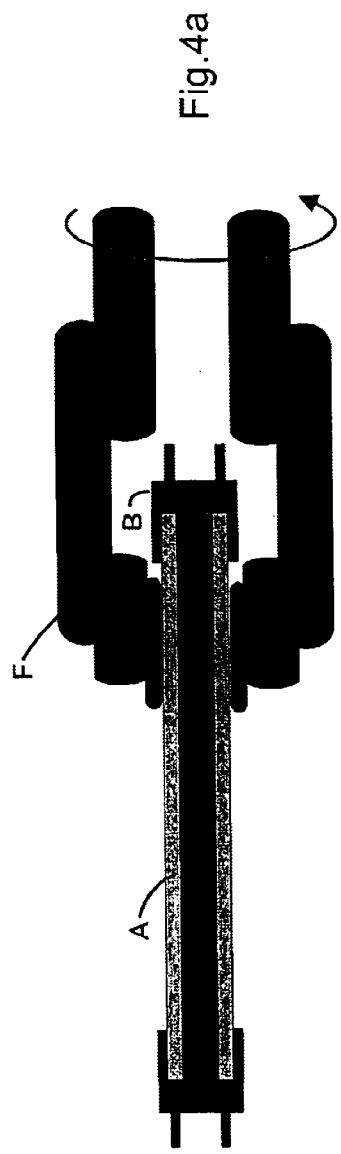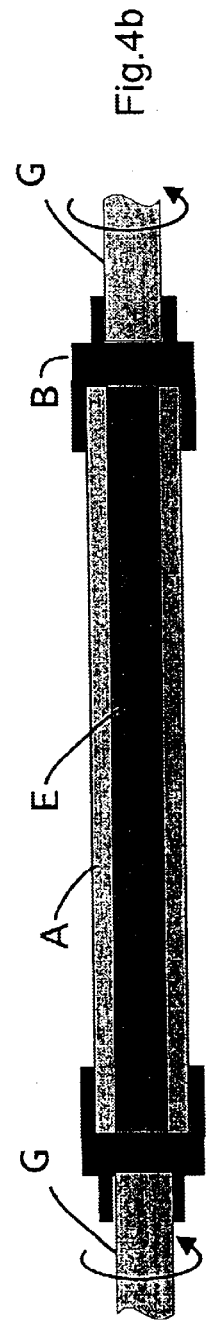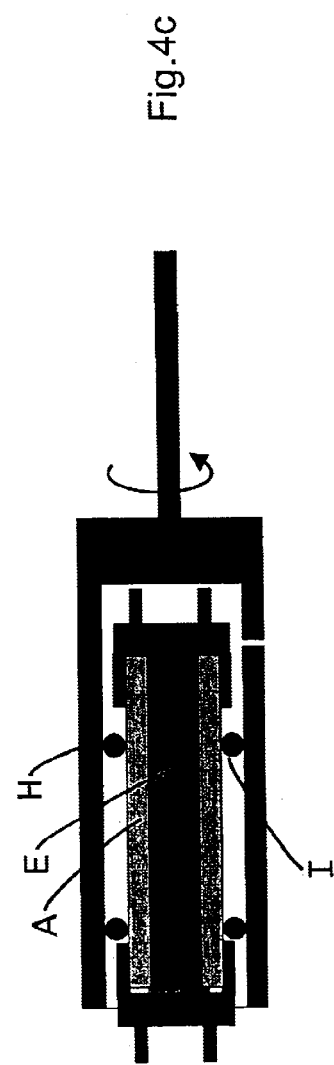

Fig.8a
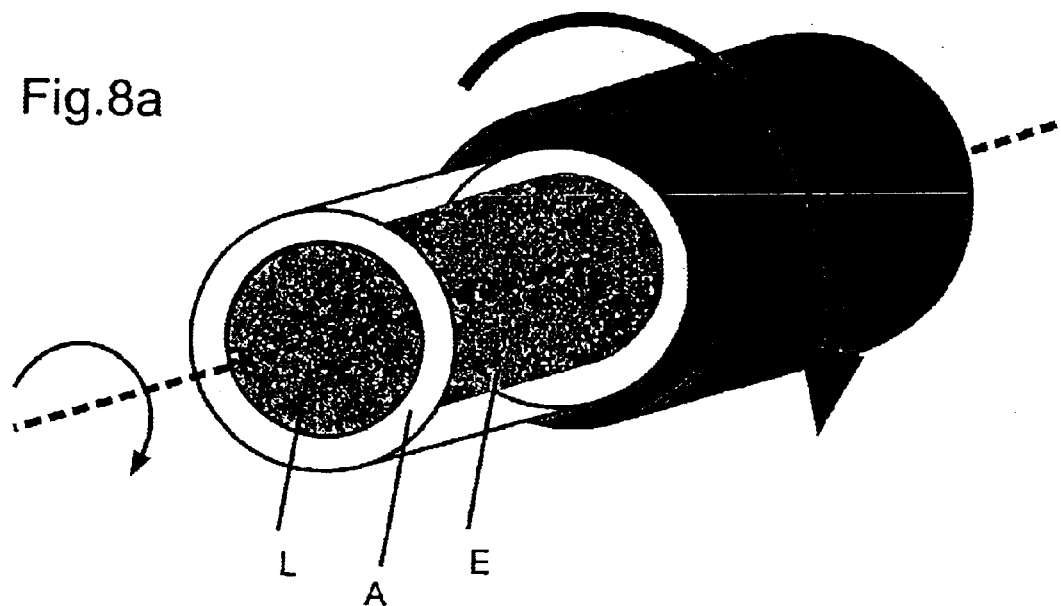
L A E
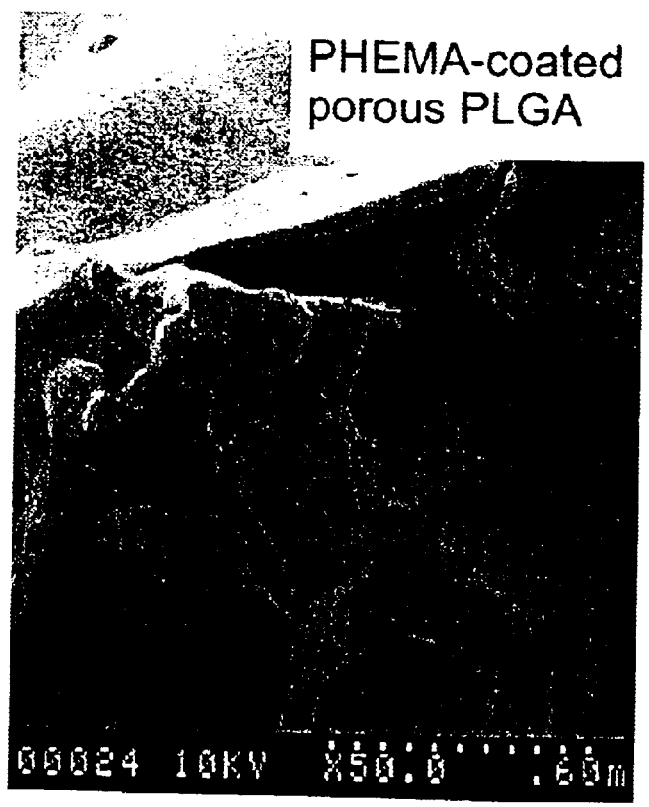
Fig.8b

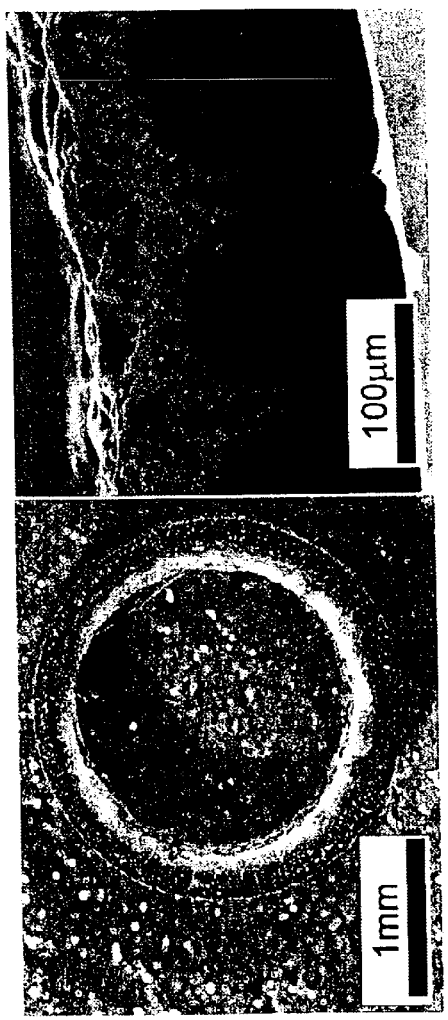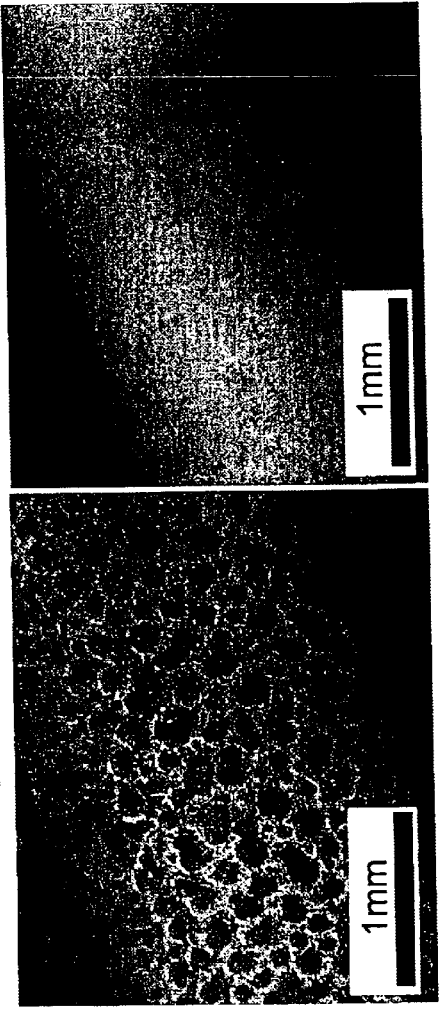
Fig.12b
Fig.12a
Fig.12d
Fig.12c

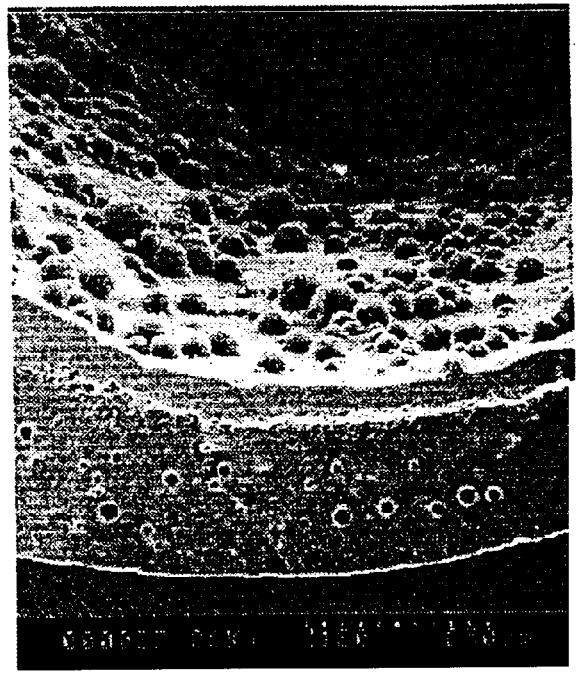
Fig. 24a
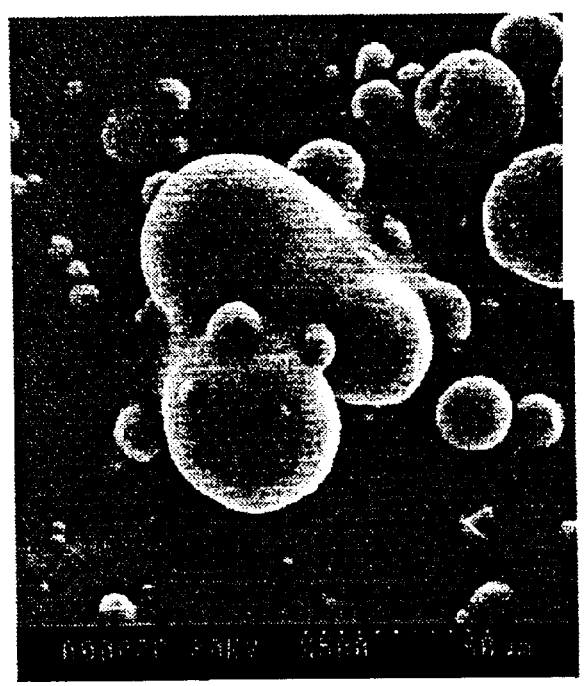
Fig. 24b
Figure 24

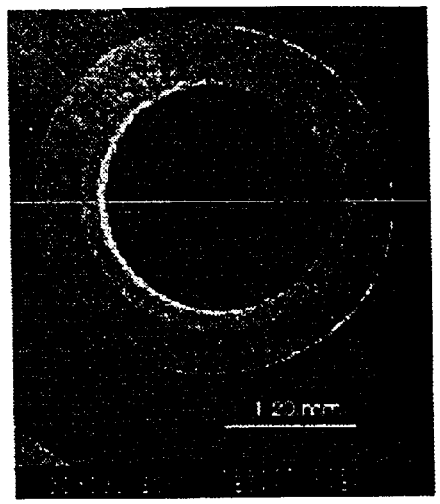
Fig. 30a
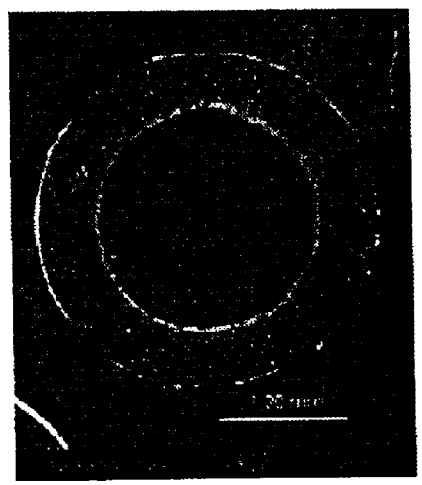
Fig. 30b
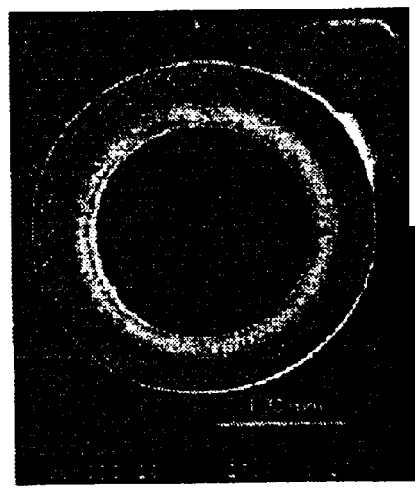
Fig. 30c
Figure 30

METHOD OF PRODUCING STRUCTURES USING CENTRIFUGAL FORCES

CROSS REFERENCE TO RELATED APPLICATIONS

This application is a continuation-in-part of U.S. utility patent application Ser. No. 10/169,948 filed on Jul. 11, 2002, now U.S. Pat. No. 6,787,090 which is a National Phase application claiming the benefit of PCT/CA01/00680 filed May 11, 2001 published in English, which further claims priority benefit from U.S. provisional patent application Ser. No. 60/203,910 filed May 12, 2000.

FIELD OF INVENTION

This invention relates to a method of manufacturing structures and particularly polymeric tubular structures and coatings with complex and unique morphologies in the walls, and on the inner and outer surfaces of the structures.

BACKGROUND OF THE INVENTION

Tubular structures and coatings have been prepared by a number of techniques, each of which has limitations for each application. For biomedical applications, a limitation is the abundant material required to prepare structures of limited size and shape, which can prove costly. For porous polymeric tubes, also known as hollow fiber membranes (HFMs), tubes with wall thicknesses on the order of hundreds of microns are prepared. There is no suitable method to prepare concentric, long HFMs, with thin walls, whether by dip-coating, spinning, or centrifugal casting, among others. As will be described in more detail, the invention comprises a process to prepare HFMs, coatings or any hollow structure, with a broad range of wall and surface morphologies, dimensions and shapes. Such wall morphologies allow HFMs to be manufactured with considerably different transport properties while maintaining similar mechanical properties.

HFMs are commonly prepared by phase inversion through an annular die (or spinneret) where the solvent/non-solvent system controls many of the resulting properties, such as morphology of the wall structure. The dimensions are controlled by the spinneret, which must be finely tuned for concentricity. While the spinning technique has a proven record commercially, it requires abundant material and requires a certain amount of art to prepare reproducible HFMs.

Centrifugal casting is a process used to make a wide number of structures, both tubular and non-concentric (U.S. Pat. Nos. 5,266,325; 5,292,515). For manufacturing tubular shapes, a cylindrical mold is partially filled with a monomer, polymer melt, or monomer solution, and with air present inside the mold, coats the periphery of the mold under centrifugal action. The material spun to the outer portion of the mold is then held in place using temperature changes (cooling), polymerization or evaporation of the solvent. For this process, two phases are present inside the mold (gas and liquid) before rotation; phase separation is not necessary for tubular formation. Wall morphologies are only attained by the addition of a porogen (salt, ethylene glycol etc.) that is leached out post-polymerization. Since a gas is required in the mold to form a tube (compared to a rod), attaining small diameter tubes with a small inner diameter on the micron scale cannot be achieved. Surface tension between the liquid and the gas inside the mold prevents miniaturization of the inner diameters for tens of centimeter length tubes.

For dip-coating, tubes are formed around a mandrel that is sequentially dipped in a polymer solution and non-solvent system, thereby coating the mandrel with the polymer via a phase inversion process. Alternately, the mandrel may be dipped in a polymer solution and the solvent left to evaporate. By these methods, the uniformity of the tube wall along the length of the tube is not well controlled.

It would therefore be very advantageous to manufacture tubes within a size regime, concentricity and with a multi-layering capability that is not presently achievable with the aforementioned methods. Furthermore, it would be desirable to have composite structures that were manufactured within a size regime, concentricity and multi-layering not presently available with the aforementioned methods. For example, composite structures allow soft tissue moduli to be matched with soft (low moduli) materials, yet to have a design that provides strength and patency, which is important to device utility.

Current coatings technologies have limitations in terms of the uniformity of the coating, thickness of the coating and coating porous materials. For example, dip-coating provides uneven coatings and the coating infiltrates the porous material. Spray-coating achieves a conformal coating that inherently coats the each pore.

It would be desirable to provide a method of producing tubular or non-tubular structures which can be used in a variety of physiological or other applications which can be produced using a wide variety of materials and which can include composites of biological materials.

SUMMARY OF INVENTION

It is an object of the present invention to provide structures, preferably tubular structures and coatings, comprising polymers and/or a combination of synthetic and naturally occurring polymers (both organic and inorganic), ceramics, metals and biological cells, tissue, matrix, proteins, in a variety of shapes including wires, fibers, particles, among others.

The present invention allows composite structures to be produced with one or a combination of synthetic and naturally occurring polymers (both organic and inorganic), ceramics, metals and biological cells, tissue, matrix, proteins, in a variety of shapes including wires, fibers, particles, among others.

In one aspect of the invention there is provided a process of producing a product, comprising:
  a) filling an interior of a mold with a mixture so that substantially all gas bubbles are displaced therefrom, the mixture comprising at least two components which can be phase separated by a phase separation agent into at least two phases;
  b) rotating said mold containing said mixture at an effective rotational velocity so that under rotation at least one of the phases deposits onto an inner surface of the mold; and
  c) forming said product by stabilizing said at least one of the phases deposited onto the inner surface of the mold.

In another aspect of the invention there is provided a product produced by a method comprising the steps of:
  filling an interior of a mold with a mixture so that substantially all gas bubbles are displaced therefrom, the mixture comprising at least two components which can be phase separated by a phase separation agent into at least two phases;
  rotating said mold containing said mixture at an effective rotational velocity so that under rotation at least one of the phases deposits onto an inner surface of the mold; and forming said product by stabilizing said at least one of the phases deposited onto the inner surface of the mold.

The product formed by this process may be removed from the mold, or alternatively remain in the mold where the product and the mold are used for various applications. The product may be a polymeric material, in which case the mixture includes either monomers or polymers or both.

The product may have a wall morphology that includes a porous structure, a gel structure or overlapping regions of porous/gel structure. The polymeric product may have a wall morphology that includes a predominantly gel morphology with porous channels running from a periphery to a lumenal side, resulting in spotting on an outer wall surface.

The product may be a composite structure comprised of: several polymers (synthetic, naturally-occurring, organic and inorganic); polymers and metals; polymers and ceramics; polymers and particles (inorganic, cells, microspheres, nanospheres, proteins, polysaccharides, glycosaminoglycans); polymers and fibers (carbon, glass, polymeric, biological, etc.).

The polymeric product may be degradable and result in soluble materials with exposure to specific conditions. The product may be degradable by hydrolytic degradation, or by non-specific (i.e. free radicals) or specific molecules, such as enzymes, which may be entrapped within the polymeric product. The polymeric product may degrade through breaking of crosslinks or the polymeric backbone.

The polymeric product may be a multi-layered product produced by repeating steps a), b) and c), at least once to produce a multi-layered product. The polymeric product may contain particulates within one or more of these steps; the position of which is influenced by the density of said particulates. These particulates may be a source of therapeutic drugs and may be inorganic, or organic in nature, be degradable, or non-degradable. These particulate may be living entities, or components of entities, such as cells. The polymeric product may be used as a reservoir for the delivery of enzymes, drugs, therapeutics, cells, cell products, genes, viral vectors, proteins, peptides, hormones, carbohydrates, growth factors or metals.

The polymeric product may contain microspheres containing preselected constituents, and wherein the product includes said microspheres distributed either uniformly or in a gradient within the wall structure of the product.

The polymeric product may contain a predetermined structure, which was inserted into the mold before said product fabrication, such as a wire, stent or mesh. The polymeric product would coat the predetermined structure, and may enhance the designed application of the said structure by releasing therapeutic agents or reducing the surface friction of said structure.

The polymeric product may be a coating on the inner wall of another tubular structure.

BRIEF DESCRIPTION OF DRAWINGS

The following is a description, by way of example only, of the method of producing tubes or coatings in accordance with the present invention, reference being had to the accompanying drawings, in which:

FIG. 1a is a cross section of a cylindrical mold used to manufacture tubes according to the present invention;

FIG. 1b is a cross section of an alternative embodiment of a cylindrical mold;

FIG. 1c is a cross section of another alternative embodiment of a cylindrical mold;

FIG. 1d is a cross section of another alternative embodiment of a cylindrical mold;

FIG. 2a is a cross section of an embodiment of a cylindrical mold with surface features along the length of the interior surface of the mold;

FIG. 2b is a cross section of an alternative embodiment of a cylindrical mold with surface features along the length of the interior surface of the mold;

FIG. 2c is a cross section of another alternative embodiment of a cylindrical mold with surface features along the length of the interior surface of the mold;

FIG. 2d is a cross section of another alternative embodiment of a cylindrical mold with surface features along the length of the interior surface of the mold;

FIGS. 3a to 3c shows the steps of filling a cylindrical mold with a liquid, FIG. 3a shows the puncturing needle (D) is used to allow exit of air from the mold, while a syringe filled with solution (E) is injected through a needle (C) that punctures the lower injection port; FIG. 3b shows the filling of the mold with the liquid solution, air exits needle (D) as the solution fills the mold, and FIG. 3c shows the mold completely filled with solution with the visible air all displaced;

FIG. 4a shows a method of rotating the cylindrical mold in which the filled mold (A) is inserted into a drill chuck (F) and rotation of the mold is commenced;

FIG. 4b shows another method of rotating the cylindrical mold in which the filled mold (A) is attached to the two ends of a lathe (G) and rotation of the mold is commenced;

FIG. 4c shows another method of rotating the cylindrical mold in which the filled mold (A) is inserted into an adapter (H) so it can be placed into a drill chuck (F) and rotation of the mold is commenced and wherein O-rings (I) maintain position of mold (A) inside the adapter (H);

FIG. 8a shows a porous plug (L) is included within the mold of FIG. 5a prior to the injection of a liquid mixture; after phase separation and gelation, the outer surface of the porous material is coated with a phase-separated mixture without any affect on the inner porosity;

FIG. 8b shows a SEM micrograph of a coating applied to a porous poly(lactic-co-glycoloic acid [75:25] material that was included within the mold of FIG. 8a prior to phase separation produced with the mixture formulation of 7% HEMA, 93% water, 0.05% APS, 0.04% SMBS, 4000 rpm (also listed in Table 1 as example 3).

FIG. 12a is an optical micrograph of a cross-section of the wall of a mixed porous/gel-like tube with radial pores made in a glass mold with the mixture formulation of 27% HEMA, 3% MMA, 70% water, 0.15% APS, 0.12% SMBS, 2700 rpm (also listed in Table 1 as example 10);

FIG. 12b shows an ESEM micrograph of a cross-section of the wall of a mixed porous/gel-like tube with radial pores made in a glass mold with the mixture formulation of 27% HEMA, 3% MMA, 70% water, 0.15% APS, 0.12% SMBS, 2700 rpm (also listed in Table 1 as example 10);

FIG. 12c shows an optical micrograph of the outer longitudinal view of a mixed porous/gel-like tube with radial pores made in a glass mold with the mixture formulation of 27% HEMA, 3% MMA, 70% water, 0.15% APS, 0.12% SMBS, 2700 rpm (also listed in Table 1 as example 10);

FIG. 12d shows an optical micrograph of of the outer longitudinal view of a mixed porous/gel-like tube with no radial pores made in a silane-treated glass mold with the mixture formulation of 27% HEMA, 3% MMA, 70% water, 0.15% APS, 0.12% SMBS, 2700 rpm (also listed in Table 1 as example 10). The hollow structure was synthesized with the same formulation as in 12a–c, but spun in a silane-treated glass mold;

FIG. 17b shows a SEM micrograph of cell-like surface patterns on the inner surface of a tube shown in FIG. 17a;

FIG. 24a shows a SEM micrograph of a cross-section of the wall of a multilayered tube containing degradable microspheres situated near the inner lumen of the tube produced with the mixture formulation of (1$^{st}$ (outer) layer 23% HEMA, 2% MMA, 75% water, 0.125% APS, 0.1% SMBS, 6000 rpm; 2$^{nd}$ (inner) layer 2% HEMA, 98% water, 1% polycaprolactone microspheres, 0.1% APS, 0.04% SMBS, 6000 rpm) (also listed in Table 2 as example 30) wherein the microspheres were added to the monomer formulation;

FIG. 24b shows a SEM micrograph of the microspheres coated in the inner surface;

FIG. 30a shows a SEM micrograph of a cross-section of a mixed porous/gel-like tube made in a cleaned glass mold with the mixture formulation of 28.05% HEMA, 4.95% MMA, 67% water, 0.165% APS, 0.162% SMBS, 2500 rpm (also listed in Table 2 as Example 36);

FIG. 30b shows a SEM micrograph of a cross-section of a mixed porous/gel-like tube made in a mold with the mixture formulation of 28.05% HEMA, 4.95% MMA, 67% water, 0.165% APS, 0.162% SMBS, 2500 rpm (also listed in Table 2 as Example 36), the hollow structure was synthesized with the same formulation as in FIG. 30a, but spun in a glass mold surface modified with 2-Methoxy (polyethyleneoxy) propyl trimethoxysilane;

FIG. 30c shows a SEM micrograph of a cross-section of a mixed porous/gel-like tube made in a mold with the mixture formulation of 28.05% HEMA, 4.95% MMA, 67% water, 0.165% APS, 0.162% SMBS, 2500 rpm (also listed in Table 2 as example 36), the hollow structure was synthesized with the same formulation as in FIG. 30a, but spun in a glass mold surface modified with N-(2-aminoethyl)-3-aminopropyl trimethoxysilane;

DETAILED DESCRIPTION OF THE INVENTION

Figure 5A:
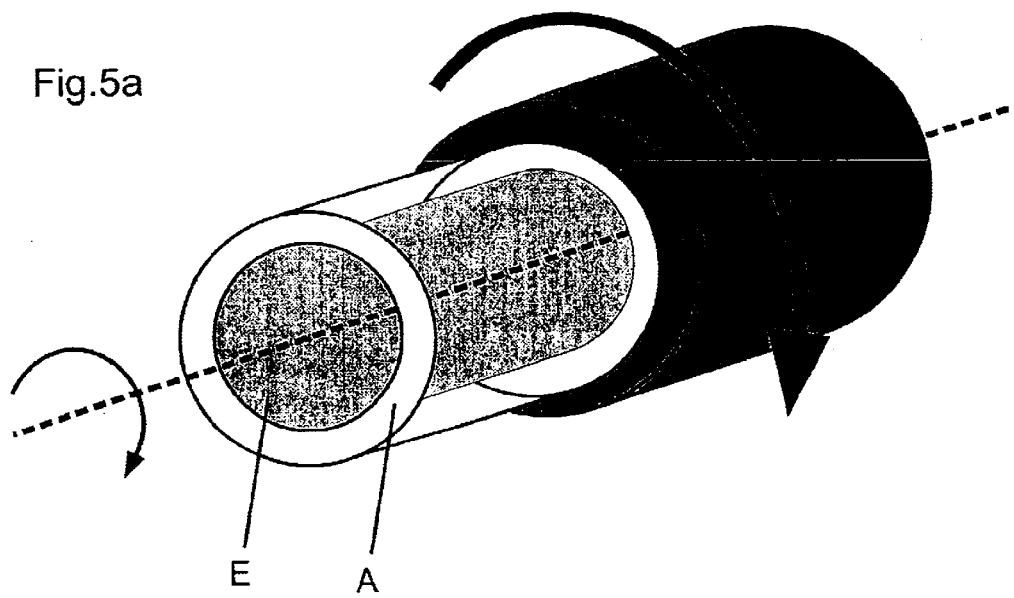
FIG. 5a is a perspective view showing a mold (A) filled with a liquid mixture (E) rotated about an axis at a suitable speed to centrifuge the phase that will eventually separate.

The forces that generate the coatings and tubular structures in this novel process are inertial forces associated with rotating a mold. A mold is filled with a mixture containing at least two liquid phase components (that are to be phase separated to produce the final product) thereby displacing substantially all of the visible gas bubbles (such as for example air) inside the mold. The mold is then rotated at some pre-determined speed, for example by being inserted into a rotating device, such as a drill chuck or lathe. The process of completely filling the interior of the mold with the liquid mixture is to ensure that all visible gas bubbles are removed from the mold. However, it will be understood that small or minute amounts of dissolved gases may still be present in the liquid mixture. The presence of these minute amounts of gas may be desirable in producing certain types of structures in that the gas may be a reactive gas serving some purpose in the phase separation process.

The phase separation process may begin immediately upon producing the mixture with separation continuing during rotation of the mold which would be the case when the phase separation is a part of the mixture. Alternatively, the phase separation process may be initiated after the mixture is formed by exposing the mixture to the phase separation agent when desired. Phase separation may be completed prior to rotation whereupon rotation simply serves to move the one phase to the inner surface of the mold or phase separation may be going on while the mold is rotating.

The rotation of the mold will send one phase to the inner surface of the mold, which will adopt the shape of the inner surface of the mold and then be stabilized to produce the product. Specifically, this separated phase must be stabilized at the surface of the mold and generally the method of stabilization will depend on the nature of the material in the separated phase. It will be understood that the phase which is driven out to the inner surface of the mold does not necessary adhere to the surface and in fact adherence is generally undesirable particularly when the product is to be removed from the mold after it is stabilized. To this end, it may be desirable to treat the inner surface of the mold to preferentially avoid adherence if this phase being separated is typically prone to forming an adhering layer. The materials from which the mold is produced may be selected to minimize adherence depending on the material of the separated phase. This would be for example when the product is to be removed from the mold after stabilization, and/or when another object is inserted into the mold onto which the phase is to be formed and stabilized. Alternatively if the intent of the process is to stabilize the product on the interior surface of the mold and use both together instead of removing the product from the mold, it may be desirable to enhance the adherence of the product on the interior surface of the mold which may be accomplished by additives added to the mixture itself which act to modify the surface or by modifying the inner surface of the mold prior to deposition. In this case the mold with product coated thereon is used in the particular application at hand.

When the products are polymeric, the components of the solution may contain monomers, macromers or polymers or any combination of two or three of these components. The phase separation process may result from changes in solubility as induced by changes in polymer chain length, changes in temperature, newly formed chemical reactants, changes in pH, exposure to light (UV, visible, IR, laser), introduction of immiscible liquids, polymer-polymer immiscibility in aqueous solutions, electric or magnetic fields. The greater density of one of the phase-separated phases results in that particular phase adopting the shape of the inner surface of the mold. It will be understood that the phase separation process may start upon mixture of the liquid components or upon filling the mold with the mixture and the phase separation process may continue during rotation of the mold or it may be complete prior to rotation of the mold.

Gelation of the separated phase may be used to fix or stabilize the morphology of the formed product and the solvent phase remains in the center of the mold. For certain types of materials, gelation of the deposited phase-separated phase can be achieved using a number of methods, including but not restricted to, continued polymerization in the separated phase (where the deposited phase comprise monomers), cooling or heating of the mold, creation of a chemical reaction product within the mold, changing the pH of the phase-separated mixture and shining a certain frequency or frequencies of light at the phase-separated mixture. By controlling rotational speed, formulation chemistry, surface chemistry and dimensions of the mold, the morphology, mechanical and porosity properties, of the resulting product can be manipulated.

It will be understood that other methods of stabilizing the denser phase may include more broadly polymerization (of which gelation is but one example), changes in temperature (either increase or decrease depending on the composition of the denser phase), light, change in pH, creation of a chemical product within the mold, changes in cationic and/or anionic concentrations, electric and magnetic fields.

Hollow structures made using the invention were synthesized in custom-built disposable molds, are shown in FIGS. 1a to 4c. Referring to FIG. 1a, the mold, which may be a glass tubing A with an inside diameter (ID) between 0.01 and 100 mm, was cut to a desired length in the order of tens of centimeters. A septum B, currently made of rubber, was slipped over each end of the glass tube to serve as an injection port. Referring to FIGS. 3a to 3c, the tubing A is filled using a needle D pushed through the upper injection port to permit the exit of gas during liquid injection. The desired mixture was injected via needle C through septum B at the lower end of the mold, displacing all of the visible gas within the mold. Withdrawing the needles D, then C results in a sealed, liquid filled mold. For concentricity and a uniform hollow structure along the length, the sealed mold was placed into the chuck of a drill that had been mounted horizontally, using a spirit level.

FIGS. 1b, 1c and 1d show alternative embodiments of differently shaped molds that may be used to produce differently shaped tubes. For example, FIG. 1d shows a mold with multiple variations in diameter along the length of the mold used to manufacture tubes with the same shape.

FIG. 2a shows a cylindrical mold containing inner surface features such as rectangular fins on the inner surface used to manufacture tubes with rectangular indentations in the outer wall of the tubes. FIG. 2b shows a cylindrical mold containing inner surface features such as convex spherical lumps on the inner surface used to manufacture tubes with concave spherical indentations in the outer wall. FIG. 2c shows a cylindrical mold containing inner surface features such as pointed dimples on the inner surface used to manufacture tubes with dimples in the outer wall of the tube. FIG. 2d shows a cylindrical mold containing inner surface features such as concave spherical lumps on the inner surface used to manufacture tubes with these features embedded in the wall of the resulting tubes. FIGS. 25a, b and c show a mold 60 that results in a non-concentric hollow structure that is corrigated on one side, and smooth on the other, and contains spherical dimples along the length of the structure. In all these embodiments the surface features can be of a symmetrical or non-symmetrical order, and different surface features can be used in any combination.

The inner surface of the mold 60 can be modified using a surface treatment, physical or chemical, that affects the morphology of the wall of the hollow structure. For example, as the separated phase can be liquid-like in nature, it can be induced to bead, and form droplets on the inner surface, thereby influencing the wall morphology. Similarly, the desired surface treatment can allow the separated phase to spread across the inner surface, also influencing the wall morphology. Similarly the surface treatment can control the ratio of porous to gel-like material in the wall morphology.

FIGS. 4a, 4b and 4c show various schemes for rotation of the filled mold (A). In FIG. 4a the mold A is inserted into a drill chuck (F) and rotation of mold is commenced. In FIG. 4b the filled mold (A) is attached to the two ends of a lathe (G) and rotation of the mold is commenced. In FIG. 4c the filled mold (A) is inserted into an adapter (H) so it can be placed into a drill chuck (F) and rotation of the mold is commenced. O-rings (I) maintain position of mold (A) inside the adapter (H).

Figure 5B:
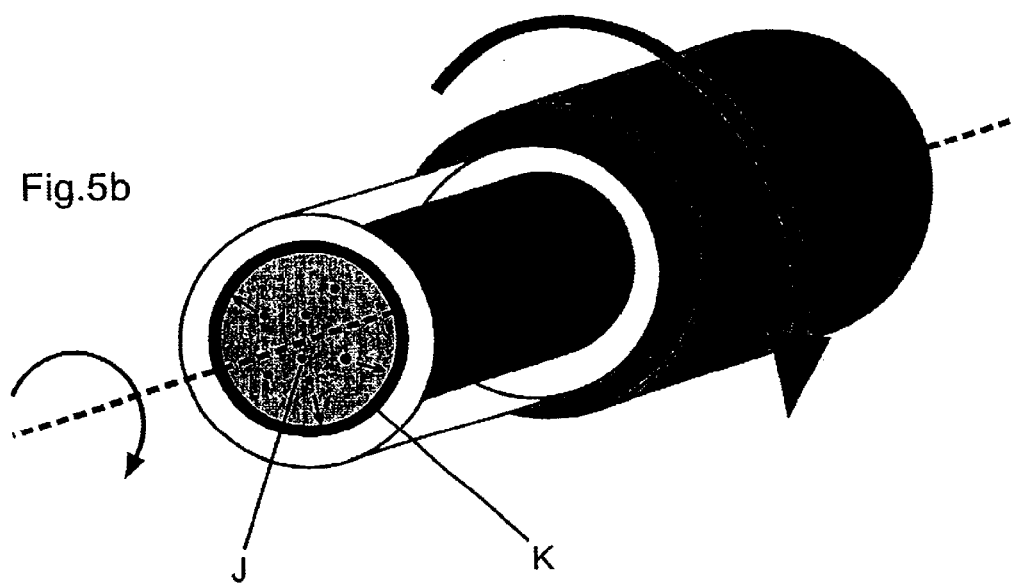
FIG. 5b shows the mixture (E) of FIG. 5a beginning to phase-separate during rotation, the dense phase (J) is centrifuged to the periphery of the mold where it adopts the shape of the inner surface of the mold (K)

FIGS. 5a and 5b show the process of phase separation during rotation of the mold. In FIG. 5a the mold (A) filled with a mixture (E) is rotated about an axis at a suitable speed to centrifuge the phase that will eventually separate. FIG. 5b shows the mixture beginning to phase-separate during rotation. The dense phase (J) is centrifuged to the periphery of the mold where it adopts the shape of the mold (K).

It will be understood by those skilled in the art that the present method is not restricted to cylindrical molds or producing tubes therefrom. Any hollow structure may be used as a mold as long as it can be rotated about some axis to utilize centrifugal forces.

With the rotating mold containing the separated phases, the more dense phase(s) are forced to the inner surface of the mold. Phase separation may result in either liquid-liquid or viscoelastic solid-liquid interfaces within the mold, while the mold is static or rotating. Phase separation can be induced using a range of different techniques and environmental changes. The addition of a propagating radical to a monomer solution can induce phase separation, as can changes in temperature, pH, exposure of the mold to light, introduction of immiscible liquids, electric and magnetic fields.

One or more of the phases will be forced to the periphery if the densities of the phases are different. The phase-separated particles then gel together, through covalent or physical bonding, to form a three-dimensional network between the separated phase(s). The gelation of particles may commence at a finite time after the onset of phase separation within the process of the invention.

A porous material can have an outer coating applied to it using this technology. Prior to the injection of a mixture into the mold, a plug of porous material is inserted into the mold (FIG. 8a). After insertion of the porous structure into the mold, a mixture is injected into the mold and rotated at the desired speed. The phase-separated phase is centrifuged through the pores of the inserted plug, and form a structure on the outer surface of the porous plug, therefore sealing the material, without blocking the internal pores. A porous material may also be a hollow structure, and the polymeric material coats the hollow structure (FIG. 28) discussed hereinafter.

In a preferred embodiment of the present invention the mixture includes at least two or more phases, one being a monomer, macromer or polymer, and the other a solvent.

For mixtures containing monomer to be initiated, the initiation agent may be free radical initiators, thermal or UV initiators and redox initiators or ionic initiators. Examples of initiators include ammonium persulfate or potassium persulfate with sodium metabisulfite, or tetramethylethylene diamine or ascorbic acid, azonitriles and derivatives thereof, alkyl peroxides and derivatives thereof, acyl peroxides and derivatives thereof, hydroperoxides and derivatives thereof; ketone peroxides and derivatives thereof, peresters and derivatives thereof and peroxy carbonates and derivatives thereof.

The mixture could also include a cross-linking agent depending on the structure of the final product that is desired and the polymer material that is formed. The crosslinking agent may be a multifunctional molecule with at least two reactive functionalities and includes multi-functional methacrylates or multi-functional acrylates, multi-functional acrylamides or multi-funtional methacrylamides, or multi-functional star polymers of polyethylene glycol and preferably, but not limited to, one of ethylene glycol dimethacrylate (EDMA), hexamethylene dimethacrylate (HDMA), poly(ethylene glycol) dimethacrylate, 1,5-hexadiene-3,4-diol (DVG), 2,3-dihydroxybutanediol 1,4-dimethacrylate (BHDMA), 1,4-butanediol dimethacrylate (BDMA), 1,5-hexadiene (HD), methylene bisacrylamide (MBAm) multi-functional star polymers of poly(ethylene oxide), oligopeptidic crosslinkers, multifunctional proteins and derivatives thereof; or combinations thereof.

An exemplary, non-limiting list of monomers that may be in the mixture includes any one of acrylates, methacrylates, and derivatives thereof such as, but not limited to, 2-hydroxyethyl methacrylate, methyl methacrylate, 2-polyethylene glycol ethyl methacrylate, ethyl acrylate, 2-hydroxyethyl acrylate, acrylic acid, methacrylic acid, 2-chloroethyl methacrylate, butyl methacrylate, glycidyl methacrylate, hydroxypropyl methacrylate; acrylamides and derivatives thereof such as, but not limited to, methacrylamide, hydroxypropyl methacrylamide, N,N-diethyl acrylamide, N,N-dimethyl acrylamide, 2-chloroethyl acrylamide, 2-nitrobutyl acrylamide, N-vinyl pyrrolidone, acenaphthalene, N-vinyl acetamide, phenyl-acetylene, acrolein, methyl acrolein, N-vinyl pyridine, vinyl acetate, vinyl chloride, vinyl fluoride, vinyl methyl ketone, vinylidene chloride, styrene and derivatives thereof, propene, acrylonitrile, methacrylonitrile, acryloyl chloride, allyl acetate, allyl chloride, allylbenzene, butadiene and derivatives thereof, N-vinyl caprolactam, N-vinyl carbazole, cinnamates and derivatives thereof, citraconimide and derivatives thereof, crotonic acid, diallyl phthalate, ethylene and derivatives thereof such as, but not limited to 1,1 diphenyl-ethylene, chlorotrifluoro-ethylene, dichloroethylene, tetrachloro-ethylene; fumarates and derivatives thereof, hexene and derivatives thereof, isoprene and derivatives thereof such as, but not limited to isopropenyl acetate, isopropenyl methyl ketone, isopropenylisocyanate; itaconate and derivatives thereof; itaconamide and derivatives thereof; diethyl maleate, 2-(acryloyloxy)ethyl diethyl phosphate, vinyl phosphonates and derivatives thereof, maleic anhydride, maleimide, silicone polymers, and derivatives thereof; polysaccharides and derivatives thereof; carbohydrates and derivatives thereof; peptides and protein fragments and derivatives thereof; chitosan and derivatives thereof; alginate and derivatives thereof; and any combination thereof.

An exemplary, non-limiting list of polymers that may be in the mixture includes any of polyacrylates, polysaccharides and derivatives thereof, such as, but not limited to glycidyl methacrylated derivatized dextran, 2-hydroxyethyl methacrylate-derivatized dextrans, dextran methacrylate, dextran acrylates, carbohydrates and derivatives thereof, polysulfone, peptide sequences, proteins, oligopeptides, collagen, fibronectin, laminin, polymethacrylates such as but not limited to poly(methyl methacrylate), poly(ethoxyethyl methacrylate), poly(hydroxyethylmethacrylate; polyvinyl acetates polyacetates, polyesters, polyamides, polycarbonates, polyanhydrides, polyamino acids, such as but not limited to poly(N-vinyl pyrrolidinone), poly(vinyl actetate), poly(vinyl alcohol, poly(hydroxypropyl methacrylamide), poly(caprolactone), poly(dioxanone) polyglycolic acid, polylactic acid, copolymers of lactic and glycolic acids, and polytrimethylene carbonates, poly (butadiene), polystyrene, polyacrylonitrile, poly (chloroprene), neoprene, poly(isobutene), poly(isoprene), polypropylene, polytetrafluoroethylene, poly(vinylidene fluoride), poly(chlorotrifluoroethylene), poly(vinyl chloride), poly(oxymethylene), poly(ethylene terephthalate), poly(oxyethylene) poly(oxyterephthaloyl), polyamides such as but not limited to, poly[imino(1-oxohexamethylene)], poly(iminoadipoyl-iminohexamethalene), poly(iminohexamethylene-iminosebacoyl), poly[imino(1-oxododecamethylene)], cellulose, polysulfones, hyalonic acid, sodium hyaluronate, alginate, agarose, chitosan, chitin, and mixtures thereof.

A non-limiting exemplary list of solvents in the mixture for the monomer and/or polymers includes any one of water, a neucleophilic or electrophilic molecule including, but not necessarily restricted to an alcohol and preferably ethylene glycol, ethanol, acetone, poly(ethylene glycol), dimethyl sulfoxide, dimethyl formamide, alkanes and derivatives thereof, acetonitrile, acetic acid, benzene, acetic anhydride, benzyl acetate, carbon tetrachloride, chlorobenzene, n-butanol, 2-chloroethanol, chloroform, cyclohexane, cyclohexanol, dichloromethane, diethyl ether, di(ethylene glycol), di(ethylene glycol) monomethyl ether, 1,4 dioxane, N,N, dimethyl acetamide, N,N, dimethyl formamide, ethyl acetate, formaldehyde, n-heptane, hexachloroethane, hexane, isobutanol, isopropanol, methanol, methyl ethyl ketone, nitrobenzene, n-octane, n-pentanol, propyl acetate, propylene glycol, pyridene, tetrahydrofuran, toluene, trichloroethylene, o-xylene and p-xylene, or aforementioned monomers or crosslinking agents, or mixtures thereof.

The solvent can be chosen to solubilize the monomer but not a polymer or crosslinked polymer formed from the monomer. One of the components may include a polymer dissolved in a solvent. The two phase-mixture may also be an emulsion.

In another embodiment an aqueous two-phase system is formed from two water soluble polymers, the two water soluble polymers being incompatible in solution and at least one of these polymers being crosslinkable; the crosslinkable polymer phase being emulsified in the other polymer phase. Crosslinking can be achieved chemically, with free radical or redox initiation, acid/base catalysis, heat, electrophilic or nucleophilic attack, or radiation. An advantage of this latter crosslinking is that in one step sterile hollow structures can be obtained. Further, crosslinking by UV radiation and physical crosslinking using hydrophobic tails coupled to a polymer are possible techniques. This aqueous polymer immiscibility occurs with many combinations of water-soluble polymers (e.g. combinations of dextran, poly (ethylene glycol) (PEG), poly(vinyl alcohol), poly (vinylpyrrolidone), gelatin, soluble starch or ficoll). The polymers stay in solution, but separate in two aqueous phases above a certain concentration. After emulsification, the polymer in the dispersed phase can be crosslinked under centrifugal forces to form a tube with hydrogel character. Examples of emulsion systems suitable for hollow structures includes but is not limited to: glycidyl methacrylated derivatized dextran(dex-GMA)/poly(ethylene glycol) (PEG); 2-hydroxyethyl methacrylate-derivatized dextrans (dex-HEMA)/PEG; dex-lactate-HEMA/PEG; dex-GMA/Pluronic F68; PEG-dimethacrylate (PEG-MA$_2$)/dextran with or without salt, such as $MgSO_4$; PEG-MA$_2$/cloud point agent such as $MgSO_4$; Gelatin/Poly(vinylpyrrolidone); Gelatin/dextran, among others.

In another embodiment, macromers may be used, comprising hydrophilic oligomers having biodegradable monomeric or oligomeric extensions or side chains, which biodegradable segments are terminated on the free end thereof with end cap monomers or oligomers capable of polymerization and cross linking. Biodegradation occurs at the backbone or at the crosslinks and results in fragments which are non-toxic and easily digested or excreted by the body. For example, macromers include modified dextran-oligopeptide-methacrylate or PEG-oligopeptides-acrylates where the peptide sequence may be recognized by enzymes, resulting in biodegradable segments.

In another embodiment a tapered hollow structure with changing dimensions along its length can be manufactured where the sealed mold is rotated at a predetermined angle between 0 and 90° from the horizontal plane.

In another embodiment a tapered hollow structure with changing dimensions along its length can be manufactured using a holding device such as shown in FIGS. 20a to d, which holds the sealed mold at a predetermined angle between 0 and 90° from the axis of rotation. The holder of FIGS. 20a, b, c holds a cylindrical mold 70 (shown in FIG. 20d, so it is rotated about an axis other than its long axis for producing tubes. The holding device (A) is preferably made of aluminium and has a stem (B) which is held in the rotating device. A hole drilled though the holding device at an angle (theta) from the axis of rotation permits the insertion of the mold (C). The mold is held in place by two rubber o-rings (E) and capped with two rubber septa (E). The angle of rotation will result in non-uniform wall thickness dimensions along the length of the mold.

Figure 21A:
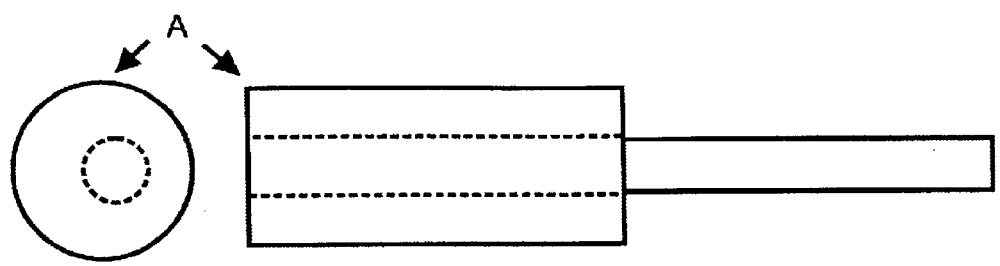
FIG. 21a is a diagram of a holding device with the centre of gravity not on the axis of rotation so the molds, when inserted into the holding device, have an axis of rotation that is parralell to the axis of rotation of the rotating device.
Figure 21B:
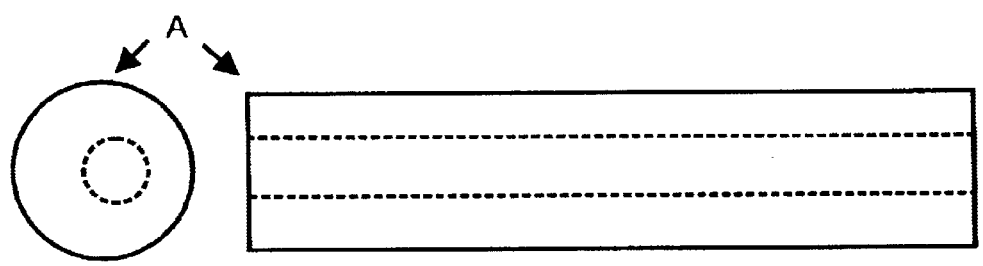
FIG. 21b is a diagram of a holding device where the mold has a centre of gravity not on the axis of rotation.

FIG. 21a is a diagram of a holding device with the centre of gravity not on the axis of rotation so the molds, when inserted into the holding device, have an axis of rotation that is parallel to the axis of rotation of the rotating device. The resultant hollow structures retrieved from such molds have non-uniform wall thicknesses as demonstrated in FIG. 21c. Alternatively the mold may have a centre of gravity not on the axis of rotation (FIG. 21b). This will also result in a hollow structure formed similar to FIG. 21c.

In another embodiment controlling the viscoelastic properties of the separated phase and/or the rotation speed can create cell-invasive hollow structures. If the separated phase has substantial elastic properties, they will not coalesce, and after gelation, the porous network between the phases is large enough for the penetration of cells into the construct.

In another embodiment multi-layered structures can be formed by repeating the process as many times as desired. After forming the first layer, the solvent can be tipped out and another mixture injected into the mold. The first layer coating the mold, effectively becomes the mold for the next coating and the second formation may penetrate into the first coating, binding them together after gelation. The multi-layered hollow structures can be manufactured using any or all of the types of tubes described in the examples, made from any material, similar or different materials, in any order required, as many times as required. A layered wall structure (ie. gel-like and porous) can be made by multiple formulations and multiple rotations or in one formulation/one rotation. The layers may result in composite polymer walls comprising polymers, polymer blends of biopolymers (such as collagen, matrix molecules, glycosaminoglycans), or any type of biodegradable material, and may contain polymer beads or spheres, colloids, drugs, living cells and other mixtures concentrically arranged in the wall radius.

Various shaped structures can be manufactured with the same methodology as Example 1 but prepared using a mold shape that is non-symmetrical along any axis. FIGS. 25a, 25b and 25c show an example of such a mold that results in a hollow structure that is corrugated on one side, and smooth on the other, and contains spherical dimples along the internal length of the structure. Any example formulation can be used to create this shape of hollow structure, in a mold with a variable diameter.

Figure 28:
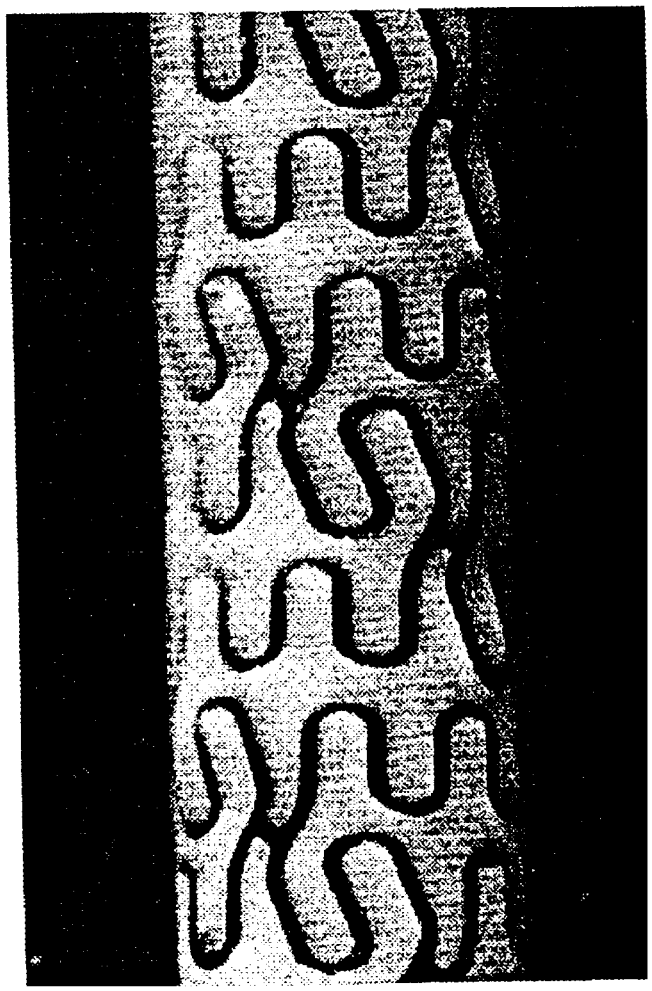
FIG. 28 shows a SEM micrograph of the length of a tube produced with the mixture formulation of 22.5% HEMA, 75% water, 2.5% MMA, 0.2% APS, 0.15% SMBS, 6000 rpm (also listed in Table 2 as Example 34), with the tube formed with a stent positioned inside the mold, this may also be considered as a coating.
Figure 29:
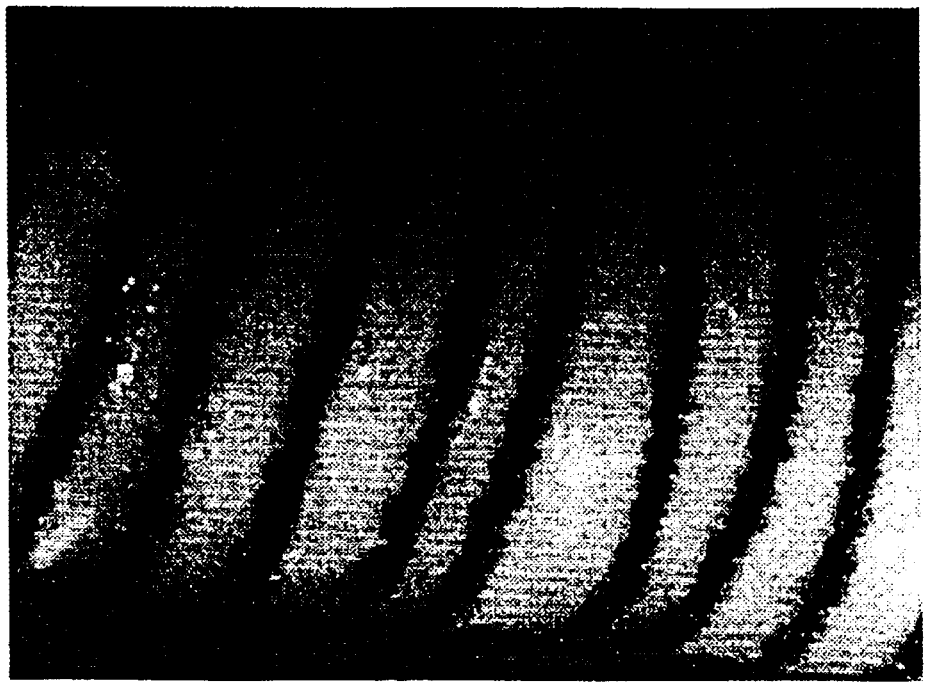
FIG. 29 shows a SEM micrograph of the length of a tube produced with the mixture formulation of 28.05% HEMA, 67% water, 4.95% MMA, 0.165% APS, 0.132% SMBS, 2500 rpm (also listed in Table 2 as Example 35), with the tube formed with a coiled manganese wire positioned inside the mold.

In another embodiment, composite hollow structures can be formed with another structure, such as but not limited to a mesh, scaffold, stent, coil and/or fiber(s) that occupies the periphery of the mold. The formulation is added to this mold as described above, resulting in composite hollow structure consisting of the hollow structure that coats the structure. Examples 34 and 35 discussed hereinafter describe such structures which are shown in FIGS. 28 and 29.

Manufacture of both physically and chemically crosslinked hollow structures are possible using this technique, as is the manufacture of both degradable and non-degradable polymer tubes. Those skilled in the art will appreciate the many applications for which the structures produced with the present method may be used. The ability to control the morphology, porosity and wall thickness of these tubes permits their use as drug delivery vehicles, when the structures are composed of physiologically acceptable materials. Drugs can also be incorporated in other materials that are incorporated into the tube, or in the tube wall itself. For example, the tube can be filled with a material, such as, but not limited to, a hydrogel, in which drugs are dispersed. Alternatively, the wall structure can serve as a reservoir for the drug or other constituent, which may be incorporated directly into the wall structure either during production of the product by including the drug or other constituent in the mixture or they can be incorporated after production by soaking the product in a solution containing the drug or constituent which is then taken up into the product (especially in the case of porous products). Alternatively, the drug or other constituent may be incorporated into another material/drug reservoir, such as microspheres or nanospheres designed to release the drug or other constituent. By multilayering with materials incorporated within each of the stages, a tube can be made with delivery of drugs to a specific location within the tube wall. FIGS. 24a and 24b shows a tube with microspheres which were included in a second layer formulation with small quantities of monomer. The drug may be delivered uniformly or in a gradient. By tuning the set-up, a gradient can be established. The drug may include, but is not limited to, enzymes, proteins, peptides, genes, vectors, growth factors, hormones, oligonucleotides, or cells.

It is also possible to produce hollow structures that allow molecules to diffuse across the wall structure. Also hollow structures can be produced that selectively allow the diffusion of molecules based on size and/or shape to diffuse across the wall structure and to allow preferential directional drug delivery. The invention can also provide hollow structures with the appropriate mechanical properties for their end use, for example to match the mechanical properties of the tissue in which they are to be implanted.

The present method can be used to produce hollow structures that have an outer gel phase and an inner porous phase. The present method can also be used to provide a hollow structure with overlapping regions of porous phase/gel phase.

A significant advantage of the present method can be used to make hollow structures of various dimensions with internal diameters from 10 $\mu$m to 100 cm. Another advantage of the present method is that it can be used to make composite hollow structures with various materials and shapes as well as thin coatings on the inner surface of other hollow structures.

The present invention will now be illustrated with several non-limiting examples. The first examples relate to 2-hydroxyethyl methacrylate polymers and copolymers that are synthesized (and crosslinked) in a rotating mold, resulting in a tube due to centrifugal forces. Such morphologies given as examples of 2-hydroxyethyl methacrylate and its copolymers are also relevant to any monomeric or polymeric system that can be induced to phase separate in a liquid-filled rotating mold. Additional examples relate to crosslinked dextran tubes and composite tubes containing microspheres, cells, particulates, spheres, coils, stents, mesh.

Applications and Utility

The product produced according to the present method may be used for a variety of applications including but not limited to aural drainage tubes, abdominal/gastrointestinal structural replacements, stents for aortic aneurysms, esophageal scaffolds, in advanced wound dressings for draining edematous fluid while releasing therapeutic agents, such as growth factors, antibiotics. Additional applications that take advantage of a tubular shape include composite catheters useful for wound care as drains, shunts and delivery matrices. Coatings applications apply to pacemaker leads, implantable sensor wire leads, wires for interventional cardiology.

More particularly, the product may be a coating on a pre-existing hollow structure. The pre-existing hollow structure is either inserted into the mold and coated with the product, or the pre-existing hollow structure is used as the mold itself. The product can contain therapeutic drugs, cells, in a gradient along length or uniformly distributed. In addition therapeutic drugs can be incorporated directly into the wall the wall of the product or they may be incorporated into microparticles (microspheres) or nanoparticles (nanospheres) which are themselves incorporated into the wall of the products. Such particles may be degradable, or non-degradable materials, and the cells may be genetically modified, or not genetically modified cells, including but not limited to olfactory ensheathing cells, fibroblasts, or oligodendrocytes, neurons, stem cells, stem cell derived cells, olfactory ensheathing cells, Schwann cells, astrocyte cells, microglia cells, or oligodendrocyte cells, endothelial cells, epithelial cells, keratinocytes, smooth muscle cells, hepatocytes, bone marrow-derived cells, hematopoetic cells, glial cells, inflammatory cells, and immune system cells to mention just a few examples. Cells encapsulated in the product can secrete molecules useful in therapeutic applications.

The product may be made of a physiologically compatible material so that it can be used as a nerve guidance channel. The nerve guidance channel can contain cell invasive scaffolds, or therapeutic drugs, cells, in a gradient along its length or uniformly distributed. In addition therapeutic drugs may be present in the wall of the product or within particles incorporated into the walls. Such particles may be degradable, or non-degradable materials, containing cells as disclosed above.

Alternatively, the mold itself may be made of a physiologically compatible material suitable as a nerve guidance channel and the product coats the inside surface of the mold. The product is effectively a coating on the inner lumen of an existing nerve guidance channel, can contain cell invasive scaffolds, or drugs, cells, in a gradient along length or not in a gradient. As mentioned above, the nerve guidance channel can contain cell invasive scaffolds, or therapuetic drugs, cells as listed above, in a gradient along its length or uniformly distributed. In addition therapeutic drugs, may be present in the wall of the product or within particles incorporated into the walls. Such particles may be made of degradable, or non-degradable materials.

The product may be used for encapsulated cell therapy applications containing genetically modified, or not genetically modified cells as discussed above. Cells encapsulated in the product can secrete molecules useful in therapeutic applications. These cells could also be used in bioreactors produced using the method of the present invention.

The product may be used as a coronary artery bypass graft or vascular graft, including those in the brain, for abdominal aortic aneurysms, and endovascular grafts. In addition therapeutic drugs, either alone embedded in the wall of the product or encapsulated within a time release drug delivery particle present in the wall of the product. Such particles may be made of degradable or non-degradable materials.

The product may be produced using materials which are physiologically compatible as replacement or artificial fallopian tubes which can contain cells, drugs and the like. The product may be used as a drainage implant for glaucoma or as a drainage implant for the lachrymal duct. These drainage implants can be produced with diameters suitable for regulating the intraocular pressure of the eye. In addition therapeutic drugs, present within particles or not, can be present in the wall of the product. The drainage implant may be used as part of a device, so as to regulate the intraocular pressure of the eye. The product may also be used as ureter and urethra replacements.

The product may also be a bioreactor for the manufacture of cell products or artificial tissues, such as intestines. The product, which may or may not be a multi-layered structure, may contain cells and remains in the mold and effectively becomes a sealed vessel where nutrients for cell growth, viability and differentiation are introduced and waste removed accordingly. The product may be a coating on a porous membrane inside the mold, and nutrients can be exposed to both sides of the product. The product can contain cell invasive scaffolds, or drugs, cells, in a gradient along length or not in a gradient. In addition therapeutic drugs, present within particles or not, can be present in the wall of the product. Such particles may be degradable, or non-degradable materials, genetically modified, or not genetically modified cells, including but not limited to the list of cells given. The bioreactor may contain degradable materials so that after a pre-determined period of time, the resultant bioreactor contains solely living cells and their extracellular matrix, and the cells may or may not have organized into a structure that can be used as an intestinal replacement.

The product may be a coating on a pre-existing hollow structure and is used as a biosensor. The pre-existing hollow structure is either inserted into the mold and coated with the product, or the pre-existing hollow structure is the mold itself. The product can have a high surface area, and improve signal to noise ratios for the application of a biosensor. The coating may have well defined surface chemistry for improvements in biosensor reproducibility.

EXAMPLE 1

2-hydroxyethyl methacrylate (HEMA) was polymerized in the presence of excess water, with a crosslinking agent, preferably, but not limited to ethylene dimethacrylate (EDMA), using a free radical initiating system and preferably an ammonium persulfate (APS)/sodium metabisulfite (SMBS) redox initiating system. A homogeneous mixture, with components detailed in Table 1, was injected into a cylindrical glass mold as described for the process involving 2-hydroxyethyl methacrylate. The homogeneous mixture was made by adding the relevant quantities of HEMA, and water into a glass vial, and mixing in the glass vial. Mixing of the solution was repeated after the appropriate amount of 10% APS solution listed in Table 1 was added. The appropriate volume of 10% SMBS solution was added to this mixture, which was mixed for an additional 30 seconds. The homogeneous monomer mixture was then drawn into a Luer-lok syringe using a 20-gauge needle. The needle was removed from the syringe and, using a new 20-gauge needle and a 0.8 $\mu$m filter, the monomer mixture was injected into the polymerization molds.

Figure 6:
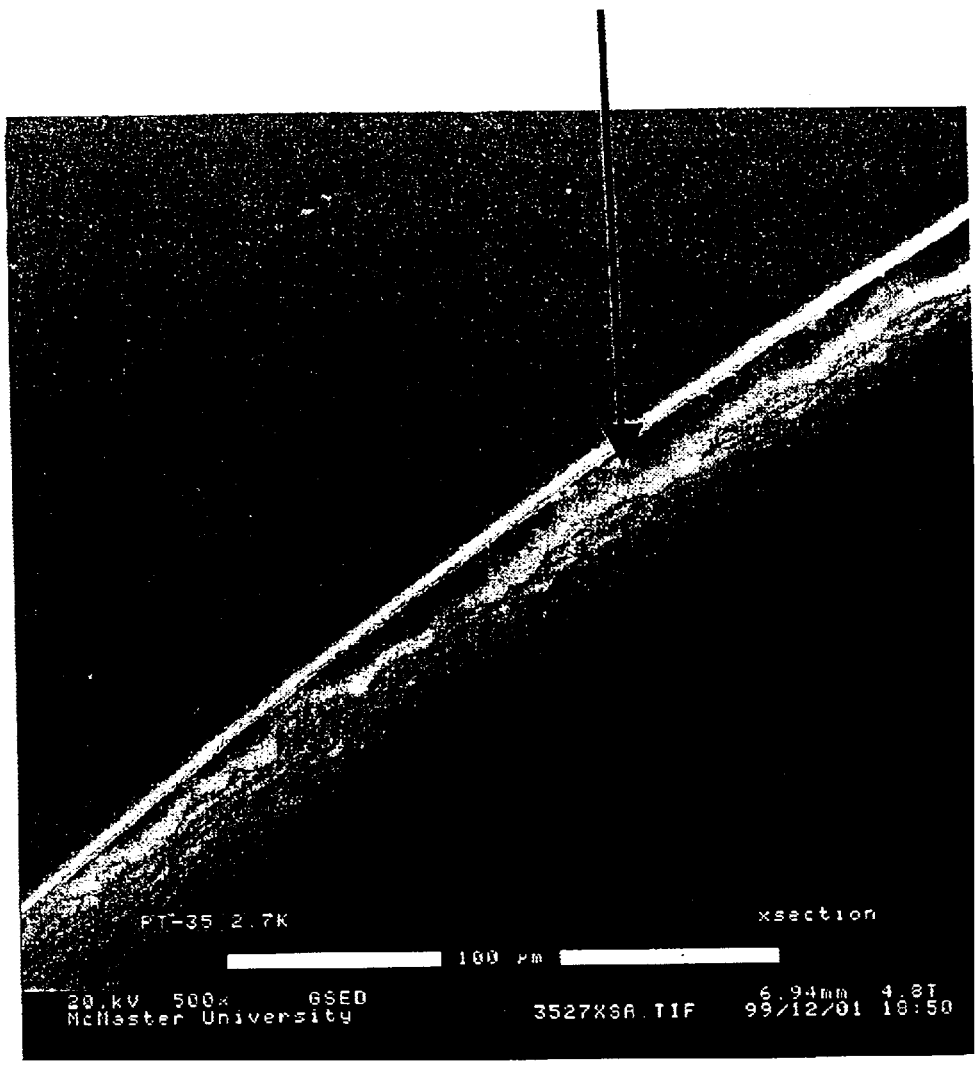
FIG. 6 shows an environmental scanning electron microscope (ESEM) micrograph of a gel-like coating on the inside of a glass mold, produced with the mixture formulation of 1% HEMA, 99% water, 0.01% APS, 0.01% SMBS, 4000 rpm (also listed in Table 1 as example 1)

The sealed mold was placed in the chuck of a RZR-1 dual range, variable speed stirring drill (Heidolph, Germany) that had been mounted horizontally, using a spirit level. The rotational speed was 2700 rpm as listed in Table 1. The resulting gel-like coating on the inner surface of the mold is shown in FIG. 6 and is approximately 10±3 $\mu$m thick. FIG. 6 shows an environmental scanning electron microscope (ESEM) micrograph of a gel-like coating on the inside of a glass mold, in which the mixture formulation was 1% HEMA, 99% water, 0.01% APS, 0.01% SMBS, 4000 rpm.

EXAMPLE 2

Figure 7B:
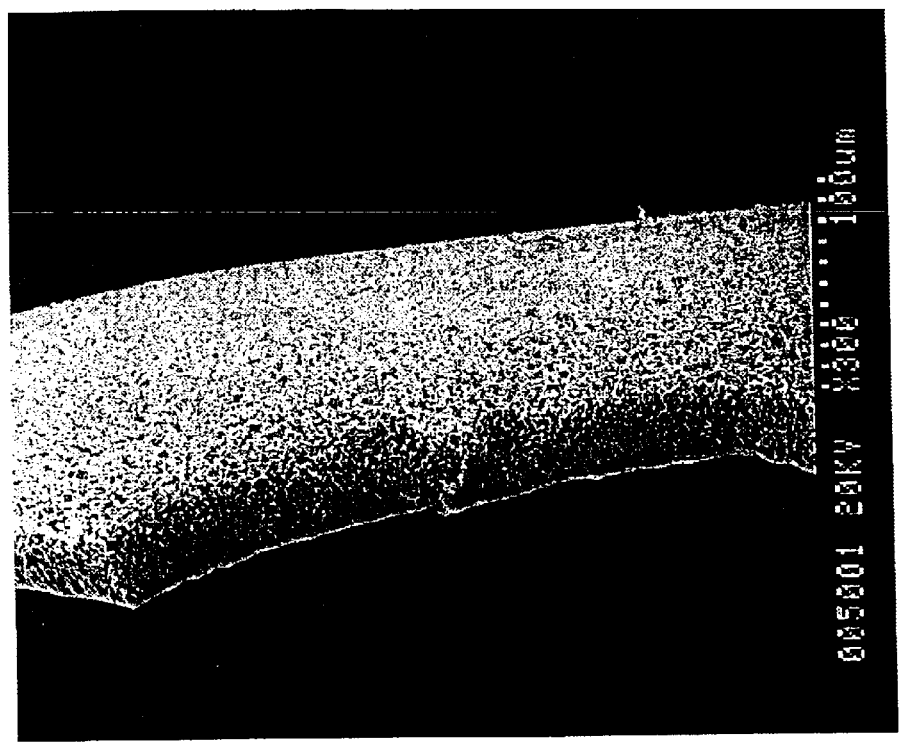
FIG. 7b shows the inner surface of a porous coating applied to the inside of a glass mold, produced with the mixture formulation of 1.9% HEMA, 0.1% PEGMA, 98% water, 0.02% APS, 0.02% SMBS, 2700 rpm (also listed in Table 1 as example 2)
Figure 7A:
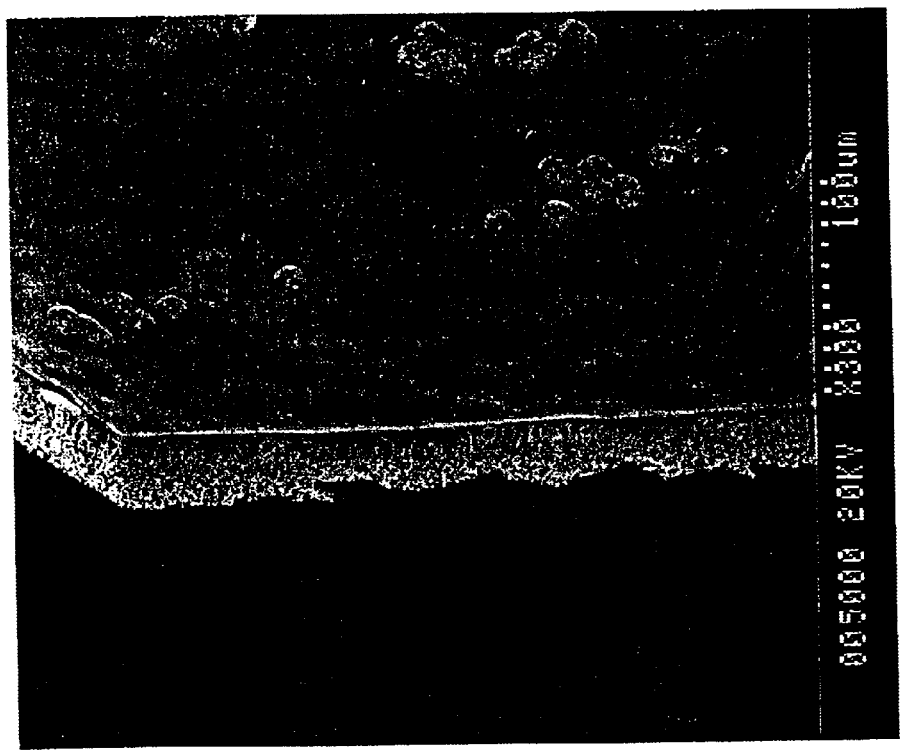
FIG. 7a shows a scanning electron microscope (SEM) micrograph of the outer surface of a porous coating applied to the inside of a glass mold, produced with the mixture formulation of 1.9% HEMA, 0.1% PEGMA, 98% water, 0.02% APS, 0.02% SMBS, 2700 rpm (also listed in Table 1 as example 2)

A coating with both gel-like and porous morphologies was prepared with the same methodology as Example 1; the monomer mixture used also included poly(ethylene glycol) methacrylate as a comonomer. The monomer mixture and rotation conditions used in Example 2 are listed in Table 1. The resulting porous material/gel-like hybrid coating on the inner surface of the mold is shown in FIGS. 7a and 7b with the outer gel-like coating (the surface that is against the inside of the mold) facing forward in FIG. 7a and the inner porous structure (the one against the water) facing forward in FIG. 7b. The thickness of the coating is approximately 30±5 $\mu$m thick. The micrograph in FIGS. 7a and 7b were taken after removing the coating from the glass mold. More specifically, FIG. 7a shows a scanning electron microscope (SEM) micrograph of the outer surface of a porous coating applied to the inside of a glass mold, in which the mixture is 1.9% HEMA, 0.1% PEGMA, 98% water, 0.02% APS, 0.02% SMBS, 2700 rpm. FIG. 7b shows the inner surface of a porous coating applied to the inside of a glass mold, in which the mixture formulation is 1.9% HEMA, 0.1% PEGMA, 98% water, 0.02% APS, 0.02% SMBS, 2700 rpm.

EXAMPLE 3

A porous material can have an outer coating applied to it using this technology. The coating that can be either gel-like or have porous morphology or both was prepared with similar methodology as in Example 1. Prior to the injection of a homogeneous mixture into the mold, a plug of porous material is inserted into the mold (FIG. 8a). Porous PLGA is manufactured using techniques previously described (Holy et al, Biomaterials, 20, 1177–1185, 1999), however the porous material may be made of any material, including polymers, ceramics, metals, composites, or combinations thereof. After insertion of the porous structure into the mold, the homogeneous mixture listed in Table 1 as Example 3 is injected into the mold and the mold rotated at the speed listed in Table 1. The resulting coated porous material removed from the mold is shown in FIG. 8b. There was no coating or blocked pores on the inside of the porous material; the only coating visible was on the outside. This example demonstrates the successful outer coating (and sealing) of a porous material without affecting the morphology of the said porous material.

EXAMPLE 4–5

Figure 9A:
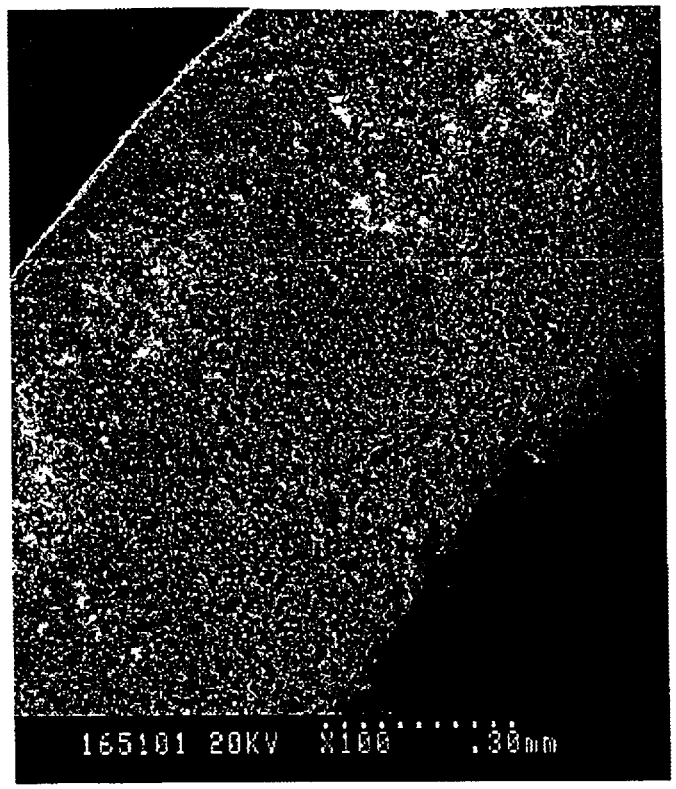
FIG. 9a shows a SEM micrograph of a cross-section of the wall of a cell-invasive, porous tube produced with the mixture formulation of 15.75% HEMA, 2.25% MMA, 82% water, 0.02% EDMA, 0.08% APS, 0.06% SMBS, 2700 rpm (also listed in Table 1 as example 4)
Figure 9B:
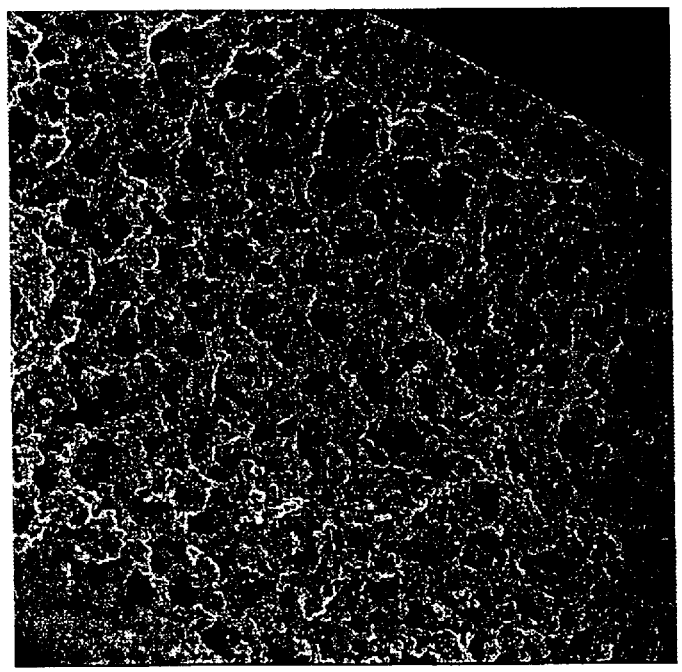
FIG. 9b is an ESEM micrograph of a cross-section of the wall of a cell-invasive, porous tube produced with the mixture formulation of 20% HEMA, 80% water, 0.02% EDMA, 0.1% APS, 0.04% TEMED, 2700 rpm (also listed in Table 1 as example 5)

A porous, cell-invasive tube can be manufactured with the same methodology as Example 1, except the monomer mixture used may include methyl methacrylate (MMA) as a comonomer. Example 5 also substitutes TEMED for SMBS as the second component in the initiating system. The monomer mixture and rotation conditions used in Examples 4–5 are listed in Table 1, and both result in cell invasive, porous tubes. In this particular instance, the use of a faster initiating system, such as, but not limited to the APS/TEMED redox system, or increased concentrations of initiator in the homogeneous mixture is beneficial to achieve the porous structure. FIGS. 9a and 9b show a porous wall morphology of Examples 4 and 5. Formation is due to sudden phase separation, in addition to viscoelastic particles separating, that do not coalesce.

EXAMPLES 6–7

A semi-porous, cell-impermeable tube can be manufactured with the same methodology as Example 1, except the monomer mixture used may include methyl methacrylate (MMA) as a comonomer. The monomer mixture and rotation conditions used in Examples 6–7 are listed in Table 1, and both result in semi-permeable non-cell invasive, tubes.

Figure 10B:
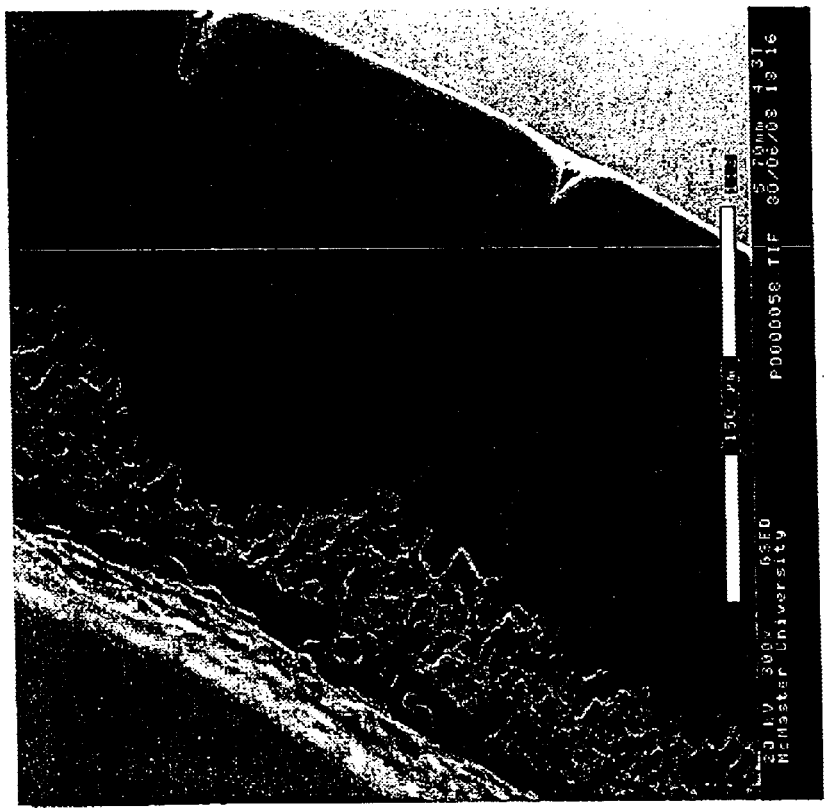
FIG. 10b shows an ESEM micrograph of a cross-section of the wall of a predominantly gel-like tube produced with the mixture formulation of 23.25% HEMA, 1.75% MMA, 75% water, 0.025% EDMA, 0.125% APS, 0.1% SMBS, 2500 rpm (also listed in Table 1 as example 7)
Figure 10A:
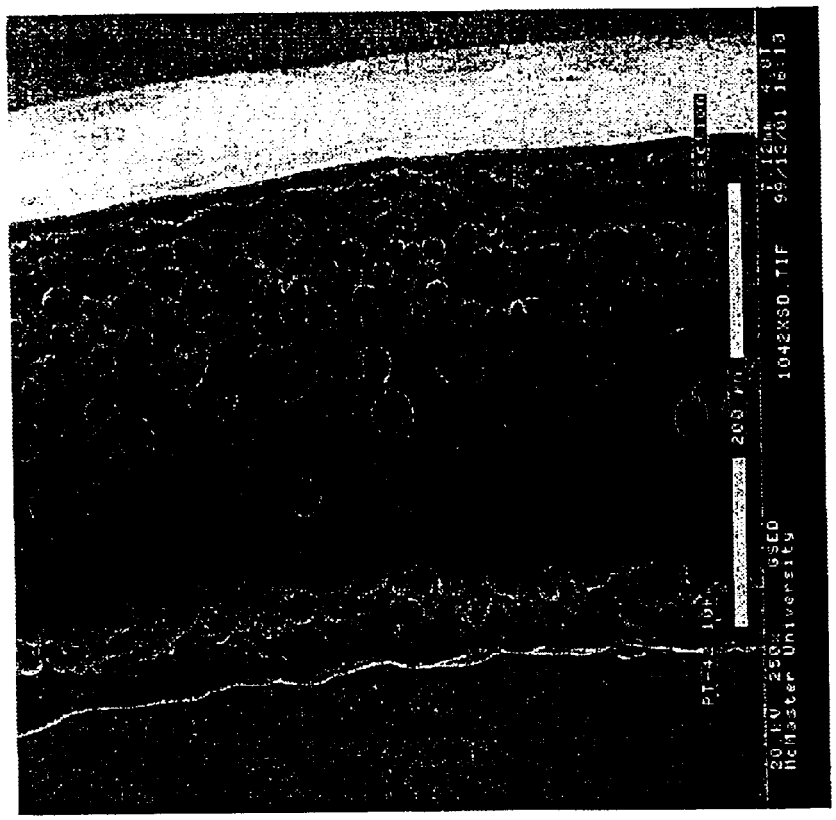
FIG. 10a shows an ESEM micrograph of a cross-section of the wall of a predominantly gel-like tube produced with the mixture formulation of 20% HEMA, 80% water, 0.02% EDMA, 0.1% APS, 0.06% SMBS, 10 000 rpm (also listed in Table 1 as example 6)

In example 6, the rotation speed is at 10,000 rpm; the high rotation speed compacts the phase separating structure against the tube wall, resulting in gel-like wall morphology with closed cell pores that affect diffusion across the wall membrane (FIG. 10a).

In the instance of example 7, the initiating system as a phase separating agent may be in a lower concentration, as slower phase separation is beneficial to achieve the non-porous, gel-like structure at lower rotation speeds (FIG. 10b).

EXAMPLES 8–9

A mixed porous/gel-like tube can be manufactured with the same methodology as Example 1, except the monomer mixture used may include MMA and/or ethylene glycol EG) which affects phase separation. The monomer mixture and rotation conditions used in Examples 8–9 are listed in Table 1, and both result in mixed porous and gel-like tubes manufactured with one polymerization. The bi-layer morphology of the cross-section of Example 8, seen in FIG. 11a, is due to the precipitation of a liquid-like phase at the start of the phase separation followed by a viscoelastic precipitate towards the end of the phase separation. Co-solvents other than water, such as EG, are therefore useful for delaying or accelerating phase separation, and therefore control the bi-layered morphology of the wall.

Figure 11B:
FIG. 11b is a SEM micrograph of a cross-section of the wall of a mixed porous/gel-like tube, produced with the mixture formulation of 27% HEMA, 3% MMA, 70% water, 0.1% APS, 0.075% SMBS, 4000 rpm (also listed in Table 1 as example 9)
Figure 11A:
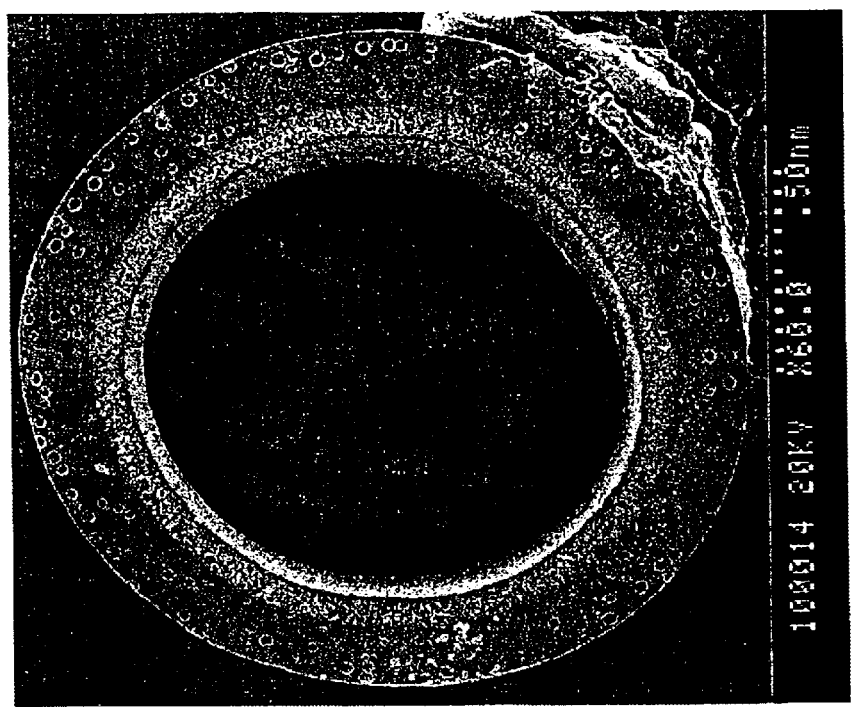
FIG. 11a shows an SEM micrograph of a cross-section of the wall of a mixed porous/gel-like tube produced with the mixture formulation of 28.3% HEMA, 58.3% water, 5.3% MMA, 8.3% ethylene glycol, 0.125% APS, 0.1% SMBS, 2700 rpm (also listed in Table 1 as example 8)

For Example 9, a porous/gel-like tube can be manufactured with the same methodology as Example 1, except faster speeds in combination with slower phase separation can induce the morphology in FIG. 11b.

EXAMPLE 10

A mixed porous/gel-like tube with radial porosity can be manufactured with the same methodology as Example 1, when the denser separating phase can be beaded as droplets on the inner surface of the rigid mold. The contact angle of the separating phase can be influenced by surface modification of the rigid mold, or changing the material of the inside of the mold. The wall morphology can therefore be influenced by the surface chemistry of the mold. The monomer mixture and rotation conditions used in Example 10 are listed in Table 1, may include co-solvents such as methyl methacrylate or ethylene glycol to influence the solubility of the separated phase. FIGS. 12a and 12b are micrographs of the porous/gel-like tube with radial porosity cross-section, with FIG. 12c showing the outer longitudinal morphology of the same formulation. The hollow structure shown in the optical micrograph in FIG. 12d was synthesized with the same formulation as Example 10, but was formed in a silane-treated glass mold. The silanating agent was Sigmacote from Sigma-Aldrich. The Sigmacote solution was drawn up into glass molds and then dried in an oven to evaporate the solvent. Contact angle studies on glass slides showed the water contact angle changed from 44.7±3°/11.6±1.8° to 47±0.3°/44±0.4° after surface modification. The glass mold was then used with the formulation listed as Example 10 in Table 1. The hollow fiber membranes had equilibrium water contents between 42% and 57%; elastic moduli between 22 kPa and 400 kPa, and diffusive permeabilities between $10^{-7}$ and $10^{-9}$ $cm^2 s^{-1}$ for vitamin B12 and dextran 10 kD. Similar mechanical strengths of the tube walls could be achieved with significantly different permeabilities, reflecting their intrinsic microstructures. The beading described in Example 10 permits highly diffusive hollow structures while maintaining good mechanical strength.

EXAMPLE 11

Figure 13B:
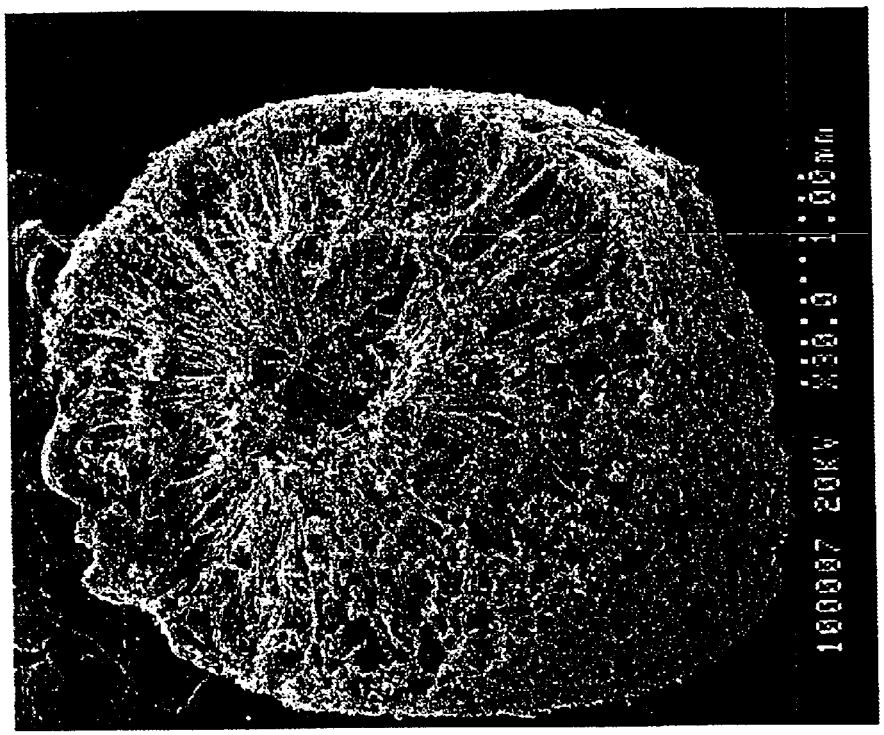
FIG. 13b shows a SEM micrograph of a cross-section of a predominantly porous wall with radial fibers produced with the mixture formulation of 2% HEMA, 98% water, 0.02% APS, 0.02% SMBS, 30 rpm (also listed in Table 1 as example 12)
Figure 13A:
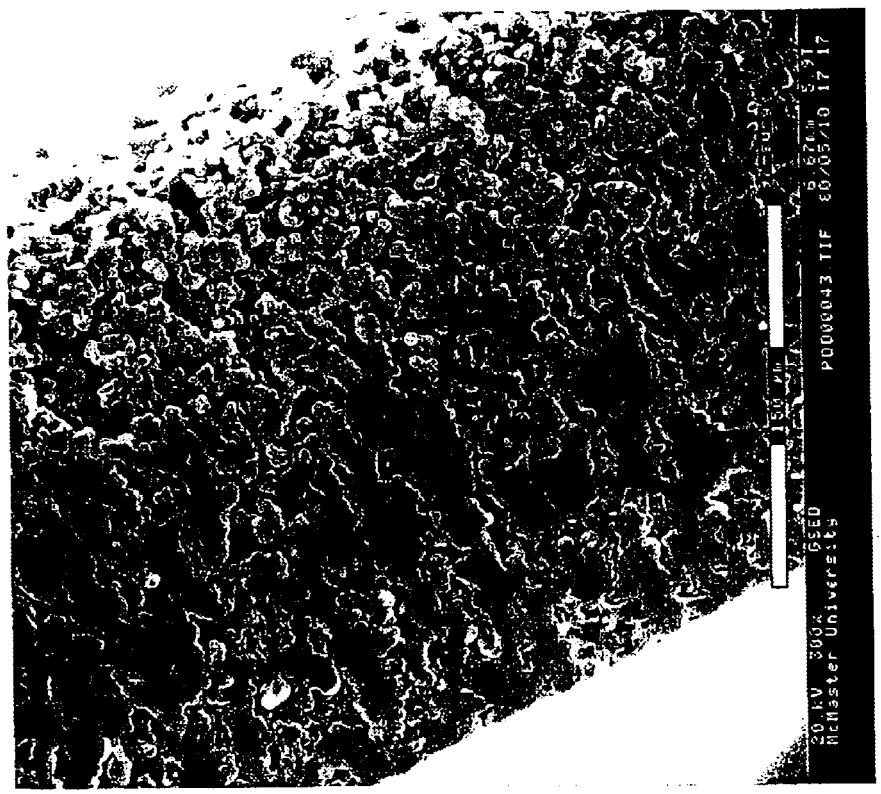
FIG. 13a shows an ESEM micrograph of a cross-section of a predominantly gel-like wall with radial pores produced with the mixture formulation of 20% HEMA, 80% water, 0.1% APS, 0.04% SMBS, 2700 rpm (also listed in Table 1 as example 11)

A porous tube with pores that are radial in nature can be manufactured with the same methodology as Example 1, with a monomer formulation mixture and rotation conditions listed in Table 1 as Example 11. The wall morphology is predominantly gel, with channels or pores that penetrate in a radial manner that does not require beading as in Example 10. An example of this morphology is shown in FIG. 13a.

EXAMPLE 12

A porous tube with fibers that are radial can be manufactured with the same methodology as Example 1, with a monomer formulation mixture and rotation conditions listed in Table 1 for Example 12. The wall morphology is predominantly space, with fibers that penetrate in a radial manner. The inner lumen of the formed hollow structure is small relative to the wall thickness and an example of this morphology is shown in FIG. 13b. In this example, the prevention of sedimentation of low concentrations was achieved with a slow rotation rate. This surprising result demonstrates the profound effect of rotation rate on the wall morphology, especially compared to Example 2 (FIGS. 7a and 7b) which has the similar monomer concentrations, but significantly different rotation rates.

EXAMPLE 13

Figure 14:
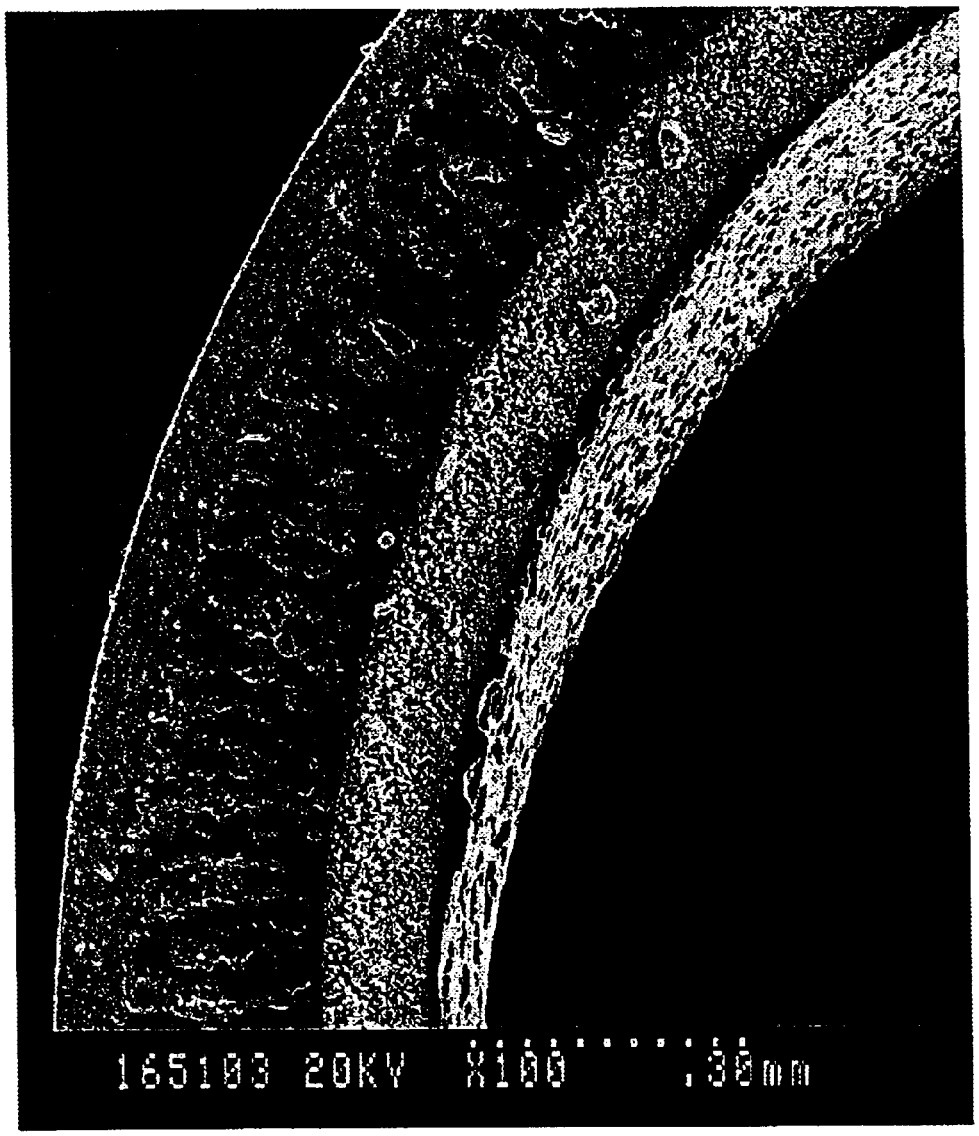
FIG. 14 shows a SEM micrograph of a cross-section of the wall of a multilayered tube produced with the mixture formulation of (1$^{st}$ (outer) layer 1.8% HEMA, 0.2% PEGDMA, 98% water, 0.002% APS, 0.002% SMBS, 2700 rpm; 2$^{nd}$ (inner) layer 27% HEMA, 3% MMA, 70% water, 0.12% APS, 0.09% SMBS, 4000 rpm.) (also listed in Table 1 as example 13)

Morphology of a cross-section of the wall of a multi-layered tube with the mixture formulation listed in Table 1 as example 13. These multi-layered tubes are can be manufactured with the same methodology as Example 1, repeated as many times as required. Example 13 in Table 1 refers to the first, outer, layer formed (o) and the second, inner formed layer (i). Multi-layered hollow structures are possible by forming one layer and using the formed hollow structure as the surface coating of the mold and the hollow structure process repeated as many times as desired. The multi-layered hollow structures can be manufactured using any or all of the types of tubes described in the examples, made from any material, similar or different materials, in any order required, as many times as required. An example is shown in FIG. 14.

EXAMPLE 14

Figure 15:
FIG. 15 shows an ESEM micrograph of the inner lumen of a tube with a smooth inner surface produced with the mixture formulation of 20% HEMA, 80% water, 0.02% EDMA, 0.1% APS, 0.04% SMBS, 2700 rpm (also listed in Table 1 as example 14)

Smooth surface morphology the inner layer of a tube with the mixture formulation listed in Table 1 as Example 14 can be manufactured with the same methodology as Example 1. A tube with a smooth inner surface is shown in FIG. 15.

EXAMPLE 15

Figure 16B:
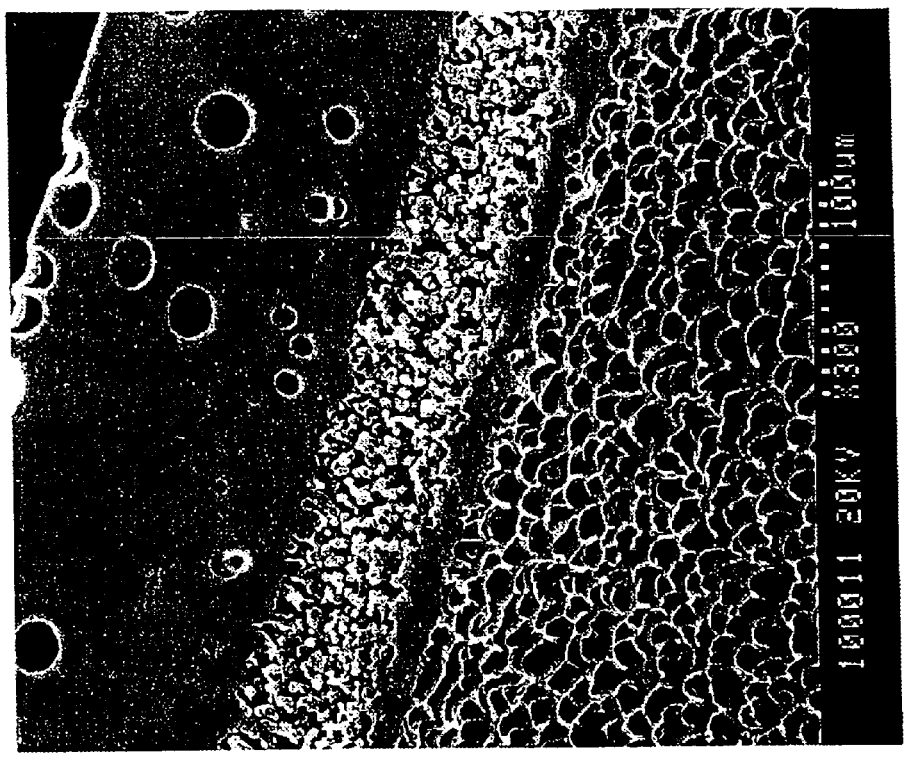
FIG. 16b shows a SEM micrograph of a lateral cross-section of the wall of the tube shown in FIG. 16a near the mold/polymer interface showing a gel-like/porous wall morphology and a dimpled/rough inner surface.
Figure 16A:
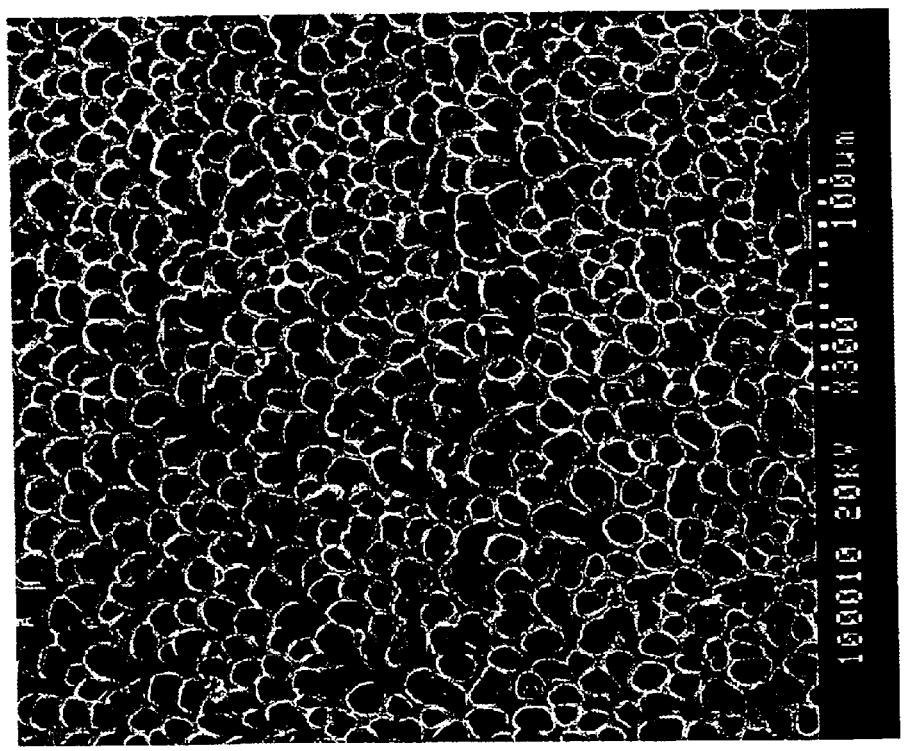
FIG. 16a shows a SEM micrograph of the inner lumen of a tube with a rough inner surface produced with the mixture formulation of 28.3% HEMA, 58.3% water, 5.3% MMA, 8.3% ethylene glycol, 0.15% APS, 0.12% SMBS, 2700 rpm (also listed in Table 1 as example 15)

Dimpled/rough surface morphology on the inner layer of a tube, which can be made using the mixture formulation listed in Table 1 as example 15, can be manufactured with the same methodology as Example 1. A tube with a dimpled/rough inner surface is shown in FIG. 16a. A lateral cross-section of the tube showing a gel-like/porous wall morphology and a dimpled/rough inner surface is shown in FIG. 16b.

EXAMPLE 16

Figure 17B:
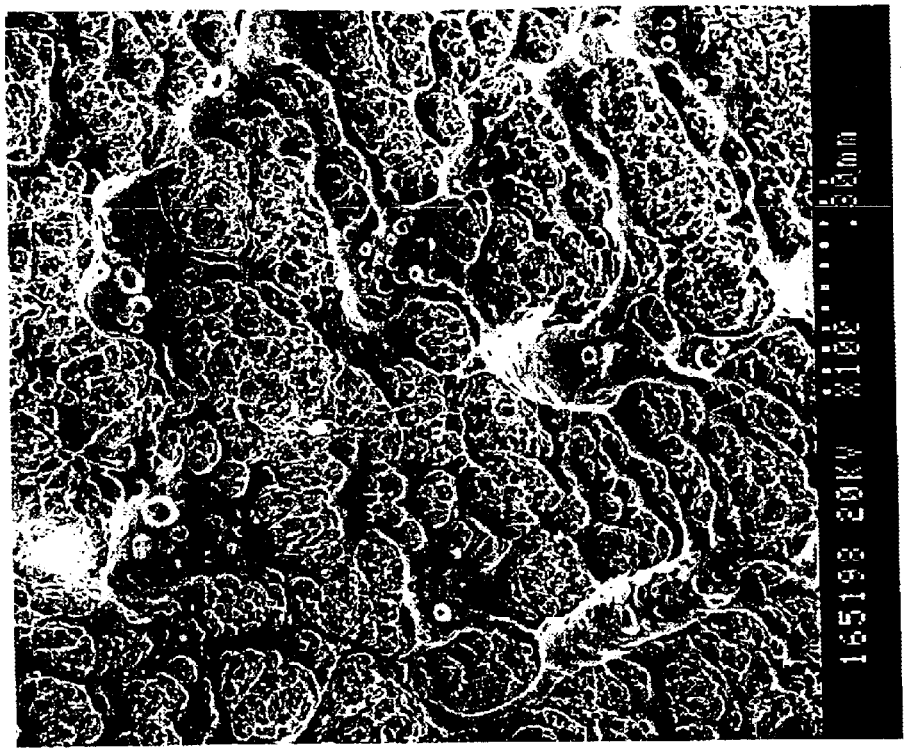
Figure 17A:
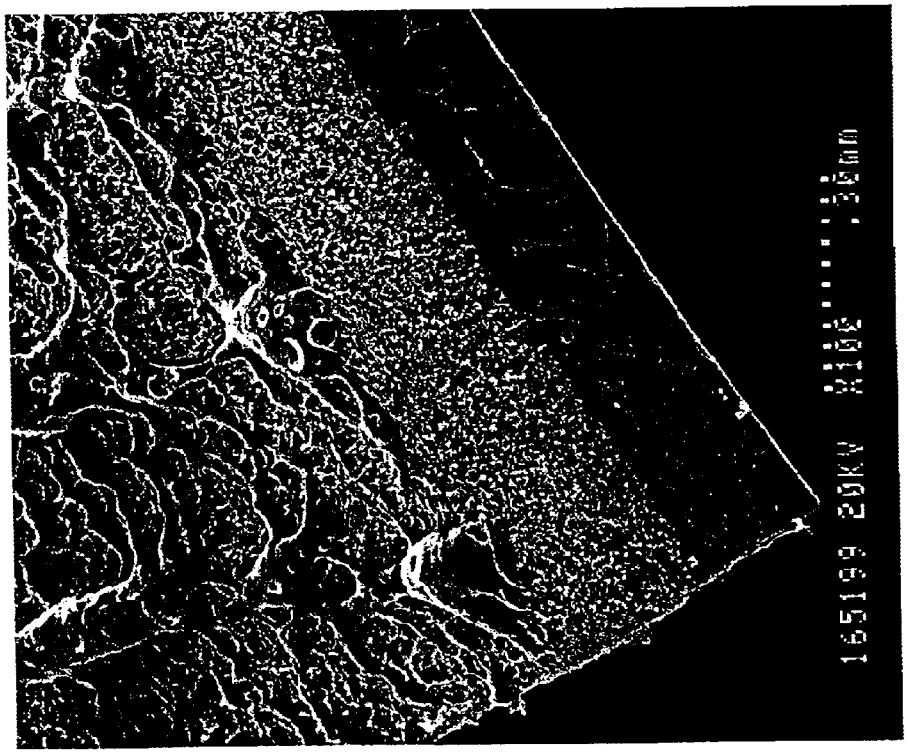
FIG. 17a shows a SEM micrograph of a lateral cross-section of the wall of the tube near the mold/polymer interface showing a gel-like/porous wall morphology and a unique cell-like surface pattern on the inner surface produced with a formulation of 27.3% HEMA, 2.7% MMA, 70% water, 0.03% EDMA, 0.12% APS, 0.09% SMBS, 4000 rpm (also listed in Table 1 as example 16)

Unique surface morphology of the inner lumen of a tube with unique cell-like surface patterns can be made using the mixture formulation listed in Table 1 as example 16 manufactured with the same methodology as Example 1. Surface morphologies such as those seen in FIG. 17a are created using this process. FIG. 17b shows such cell-like surface patterns on the inner lumen of a tube with a gel-like/porous wall morphology.

EXAMPLE 17

Figure 18:
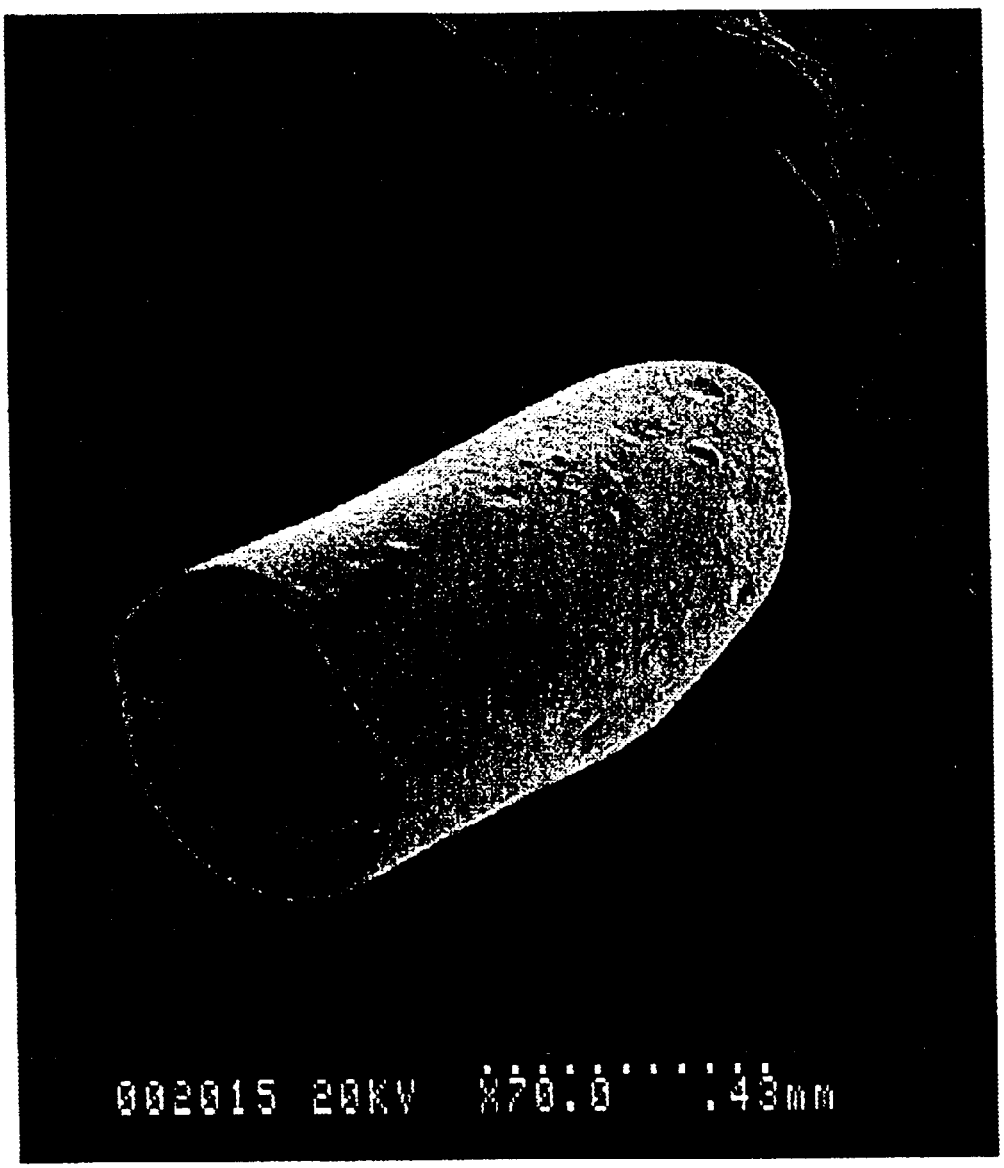
FIG. 18 shows a SEM micrograph of very small diameter micro-tubes manufactured with the mixture formulation of 22.5% HEMA, 2.5% MMA, 75% water, 0.125% APS, 0.1% SMBS, 4000 rpm (also listed in Table 1 as example 17), made in small diameter capillary tubing with an internal diameter of 450 μm.

Very small diameter micro-tubes can be manufactured with the same methodology as Example 1, except the mold size is very narrow. FIG. 18 is a tube that was manufactured from a mixture formulation listed in Table 1 as example 17 in small diameter capillary tubing with an internal diameter of 450 $\mu$m. Smaller tubing can be created by using molds with an internal diameter of 10 $\mu$m and larger.

EXAMPLE 18

Figure 19:
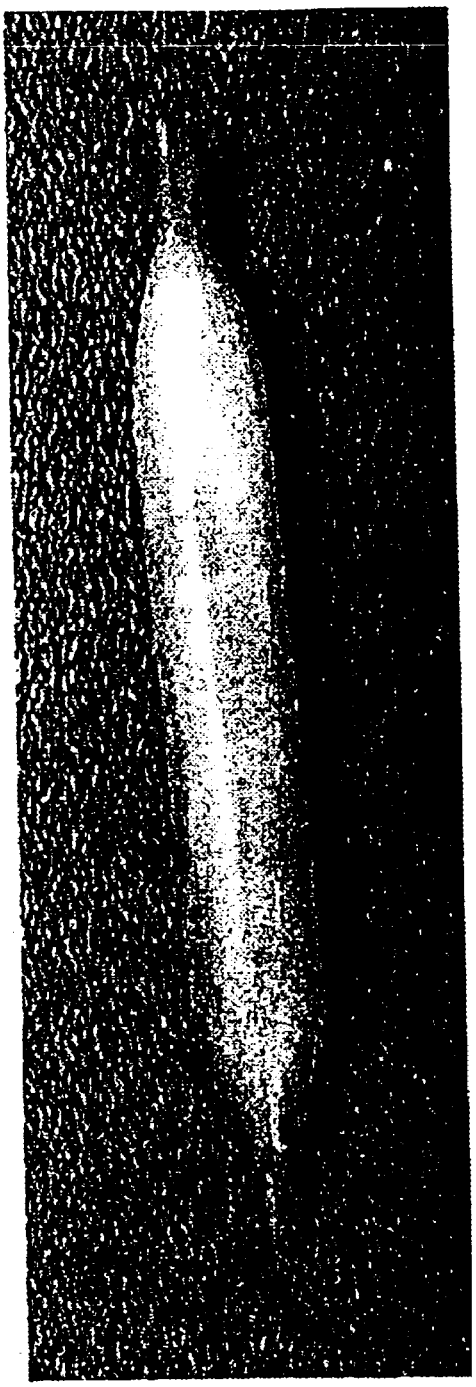
FIG. 19 is an optical micrograph of a non-uniformly shaped structure manufactured with the mixture formulation of 23.25% HEMA, 1.75% MMA, 75% water, 0.125% APS, 0.1% SMBS, 2500 rpm (also listed in Table 1 as example 17) wherein the mold size does not have a uniform internal diameter.

Various shaped structures can be manufactured with the same methodology as Example 1, except the mold size is neither cylindrical nor has a uniform internal diameter. FIG. 19 is a tube that was manufactured from a mixture formulation listed in Table 1 as example 18, in a mold with a variable diameter. Any example formulation can be used to create this shape of hollow structure.

EXAMPLE 19

A tapered hollow structure with changing dimensions along it length can be manufactured with the same methodology as example 1, except the sealed mold was placed into the chuck of a drill that had been mounted at a predetermined angle between 0 and 90° from the horizontal plane.

EXAMPLE 20

A hollow structure with variable wall thickness or holes along the length can be manufactured with the same methodology as example 1, except the sealed mold has some inner surface morphologies, such as in FIGS. 2a–d. Any example formulation can be used to create this shape of hollow structure.

EXAMPLE 21

Hollow structures can be manufactured from the liquid-liquid phase separation of a polymer solution using temperature as the phase separating agent. Poly(lactic-co-glycolic acid) was dissolved in a 87:13 (wt %) dioxane/water mixture at 60° C. to create a solution that is injected into pre-heated glass molds. After injecting in a sealed glass mold, removing all air from the mold, it was placed in the chuck of a drill at room temperature and spun at 4000 rpm. The mold was allowed to cool to room temperature, which induced liquid-liquid phase separation and gelation. The mold was then frozen and the dioxane/water mixture removed by placing in a freeze-dryer. The formed tube is then removed from the mold.

EXAMPLE 22

N-2-(hydroxypropyl) methacrylamide (HPMA) (30 vol %) was polymerized in the presence of excess acetone/dimethyl sulfoxide (DMSO) (93:7 v/v), with a crosslinking agent, preferably, but not limited to methylene bisacrylamide (1 mol %), using azobisisobutyronitrile (AIBN) as an initiating system. A monomeric sugar may or may not be also added to the polymerization mixture. The mixture was fully mixed, and injected into a cylindrical glass mold as described for Example 1 using the mixture formulation listed in Table 1 as example 22.

The sealed mold was placed in the chuck of a stirring drill that had been mounted horizontally, using a spirit level and rotated at 4000 rpm at 50° C. for 24 hours. The resulting hollow structure on the inner surface of the mold is removed from the mold.

EXAMPLE 23

Figure 20:
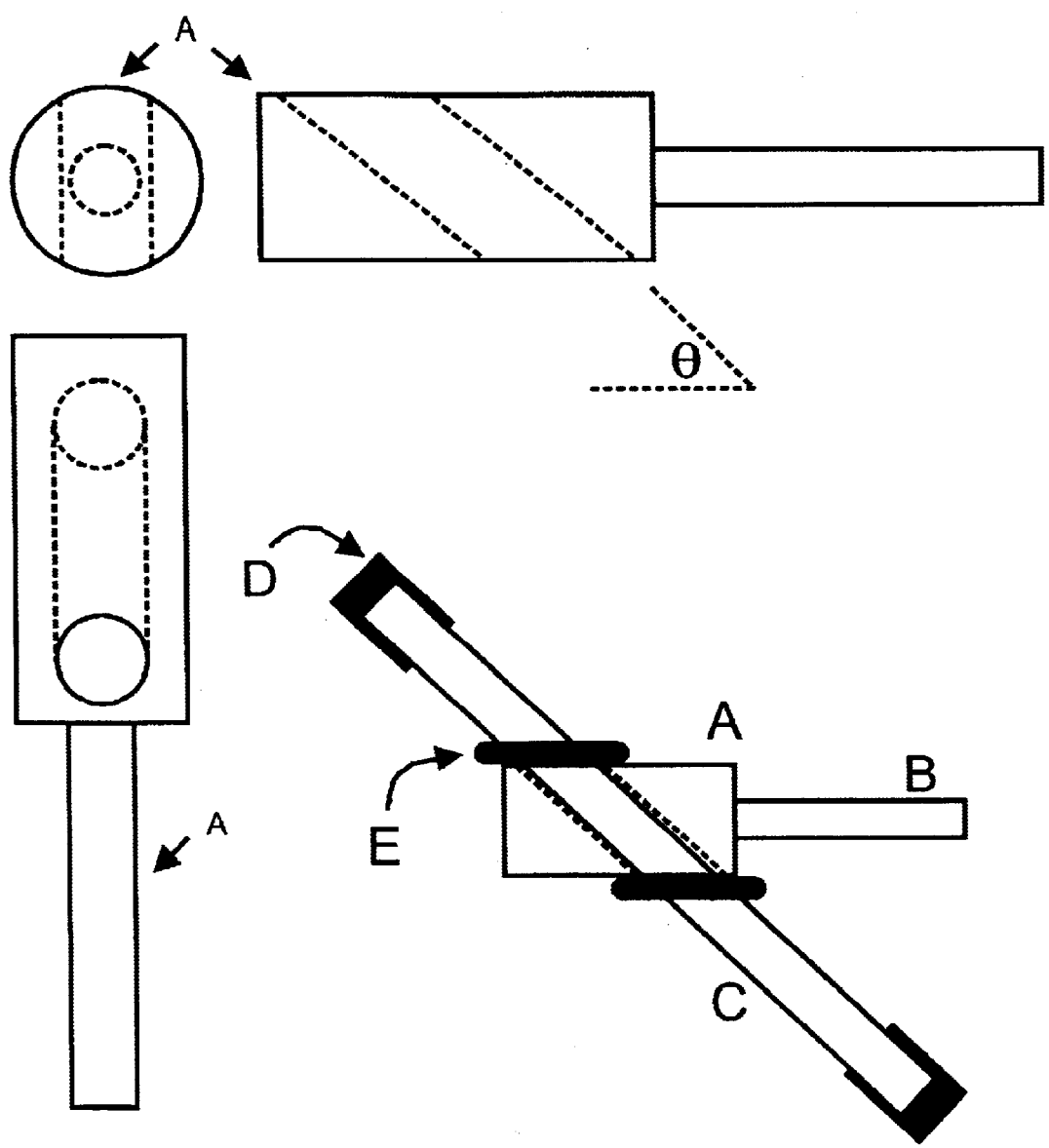
FIG. 20 is a diagram of a holding device to contain a cylindrical mold so it is rotated about an axis other than its long axis used to manufacture tubes according to the present invention.

A coating with non-uniform dimensions along the length prepared with the same methodology as Example 1, except the molds were rotated about an axis other than its long axis. Holding devices as shown in FIG. 20 were fabricated from aluminium and are designed to fit into the chuck of a drill and hold the polymerization mold at an angle from. Molds can be rotated an axis other than its long axis determined by the holding device created. The resultant coatings have tapered, non-uniform dimensions along their long axis. Any example formulation can be used to create this shape of hollow structure.

EXAMPLE 24

Figure 21C:
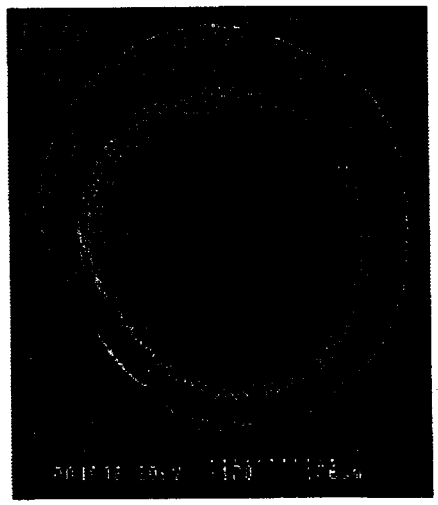
FIG. 21c shows a SEM micrograph of a hollow structure retrieved from the molds of FIG. 21a or 21b showing non-uniform wall thicknesses in its lateral cross-section.

A coating with non-uniform dimensions was prepared with the same methodology as Example 1, except the polymerization molds were rotated in a holding device with the centre of gravity not on the axis of rotation. The polymerization molds listed in Example 1 were placed into a cylindrical aluminium holding device with an offset centre (FIG. 21a or FIG. 21b) from the axis of rotation. The holding device was then inserted into the chuck of the drill and rotation commenced. The resultant coating is non-uniform in its lateral cross-section as shown in FIG. 21c. Any example formulation can be used to create this shape of hollow structure.

EXAMPLE 25

Figure 22:
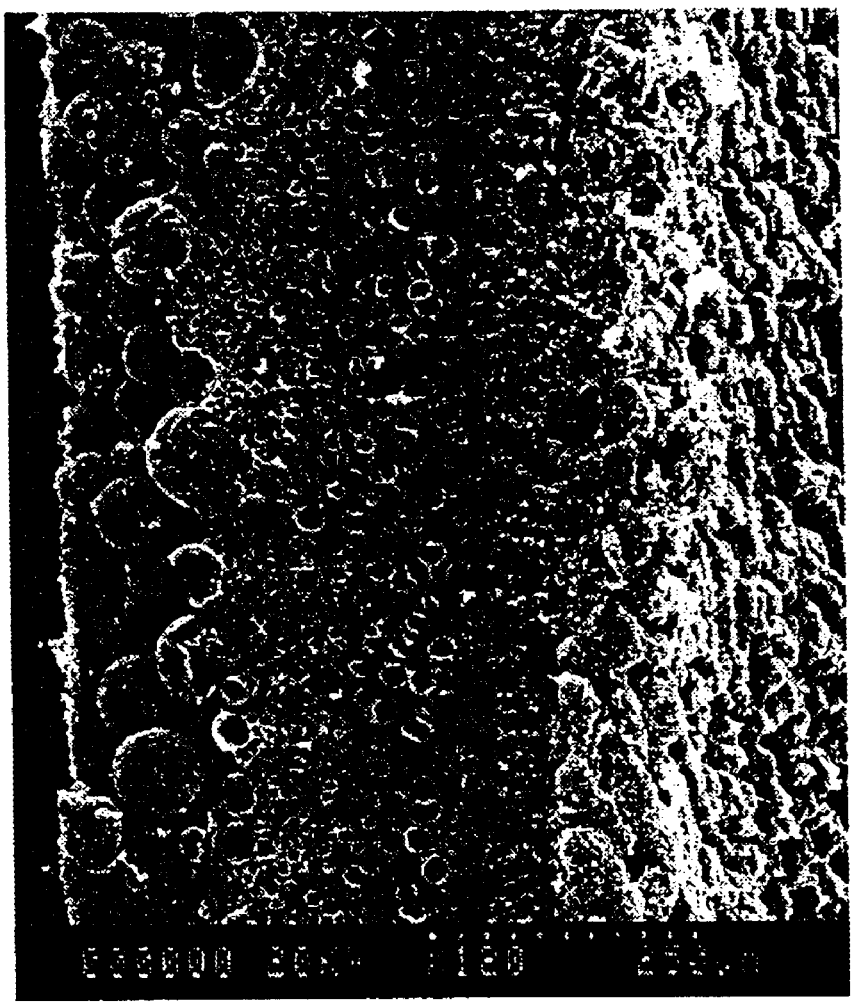
FIG. 22 shows a SEM micrograph of degradable microspheres situated in the outer lumen of a coating with the mixture formulation of 1% polycaprolactone microspheres, 19.77% HEMA, 0.02% EDMA, 79.04% water, 0.1% APS, 0.04% SMBS, 2500 rpm (also listed in Table 2 as Example 25) wherein the microspheres were added to the monomer formulation.

A coating with degradable microspheres situated in the outer lumen of the coating can be prepared with the same methodology as Example 1, except a particulate material that has greater density than the phase separated monomer component was included within the homogeneous monomer mixture. Upon rotation of the polmerization mold, the dense particulates are forced to the inner surface of the mold. When the dense, polymeric phase is gelled within the mold, a coating is formed that is shown in lateral cross-section in FIG. 22. Polycaprolactone (PCL) microspheres of average diameter 20 microns were manufactured as described in Cao et al; Biomaterials, 20, 329–339, 1999, and were added to the filtered monomer mixture in quantities outlined in Table 2. Filtering the solution was not done after the microspheres were added. Such particulate-containing tubes can be made using any material for the tube that is conducive to this manufacturing process, and using microspheres made from any biodegradable or non-biodegradable polymer that is compatable with the formulation mixture.

EXAMPLE 26

A coating with microspheres situated near the inner lumen of the coating can be prepared with the same methodology as Example 1, except a particulate material with a density between the solvent and denser phase was included within the monomer mixture. Upon rotation of the polmerization mold, the dense particulates move to the interface between the solvent and the dense polymeric phase. When the dense polymeric phase is gelled within the mold, a coating is formed with particulates fixed near the inner lumen of the coating. Such particulate-containing tubes can be made using any material for the tube that is conducive to this manufacturing process, and using microspheres made from any biodegradable or non-biodegradable polymer that is compatible with the formulation mixture.

EXAMPLE 27

A coating with degradable microspheres in a gradient along the length of the axis of rotation can be prepared with the same methodology as Example 1, except a particulate material that has greater density than the phase separated monomer component was included within the homogeneous monomer mixture and the sealed mold was placed into the chuck of a drill that had been mounted at a predetermined angle between 0 and 90° from the horizontal plane. The microspheres sediment due to gravity and upon rotation of the mold, the particulates are forced to the inner surface of the mold and then fixed in place due to the gelation of the dense polymeric phase. Polycaprolactone (PCL) microspheres of average diameter 20 microns were manufactured as described in Cao et al; Biomaterials, 20, 329–339, 1999, and were added to the filtered monomer mixture in quantities outlined in Table 2. Filtering the solution was not done after the microspheres were added. Such particulate-containing tubes can be made using any material for the coating that is conducive to this manufacturing process, and using microspheres made from any biodegradable or non-biodegradable polymer that is compatible with the formulation mixture.

EXAMPLE 28

A coating with microspheres situated in the outer lumen of the coating can be prepared with the same methodology as Example 1, except a particulate material that contains a therapuetic drug was included within the homogeneous monomer mixture. For example, molecules, such as nerve growth factor (NGF) and ovalbumin (OVA) can be encapsulated in PCL polymer microspheres using a solvent evaporation technique described in Cao et al; Biomaterials, 20, 329–339, 1999. A mixture containing microspheres is therefore injected into a sealed cylindrical glass mold as described in Example 1, except the mixture is not passed through a filter. Examples of therapeutic drugs include, but are not limited to NGF, BDNF, NT-3, NT-4/5, FGF-1, FGF-2, IGF, VEGF, CNTF, GDNF, BMP family; hormones, proteins, peptides, chemical drugs, such as neuroprotective agents.

EXAMPLE 29

Figure 23:
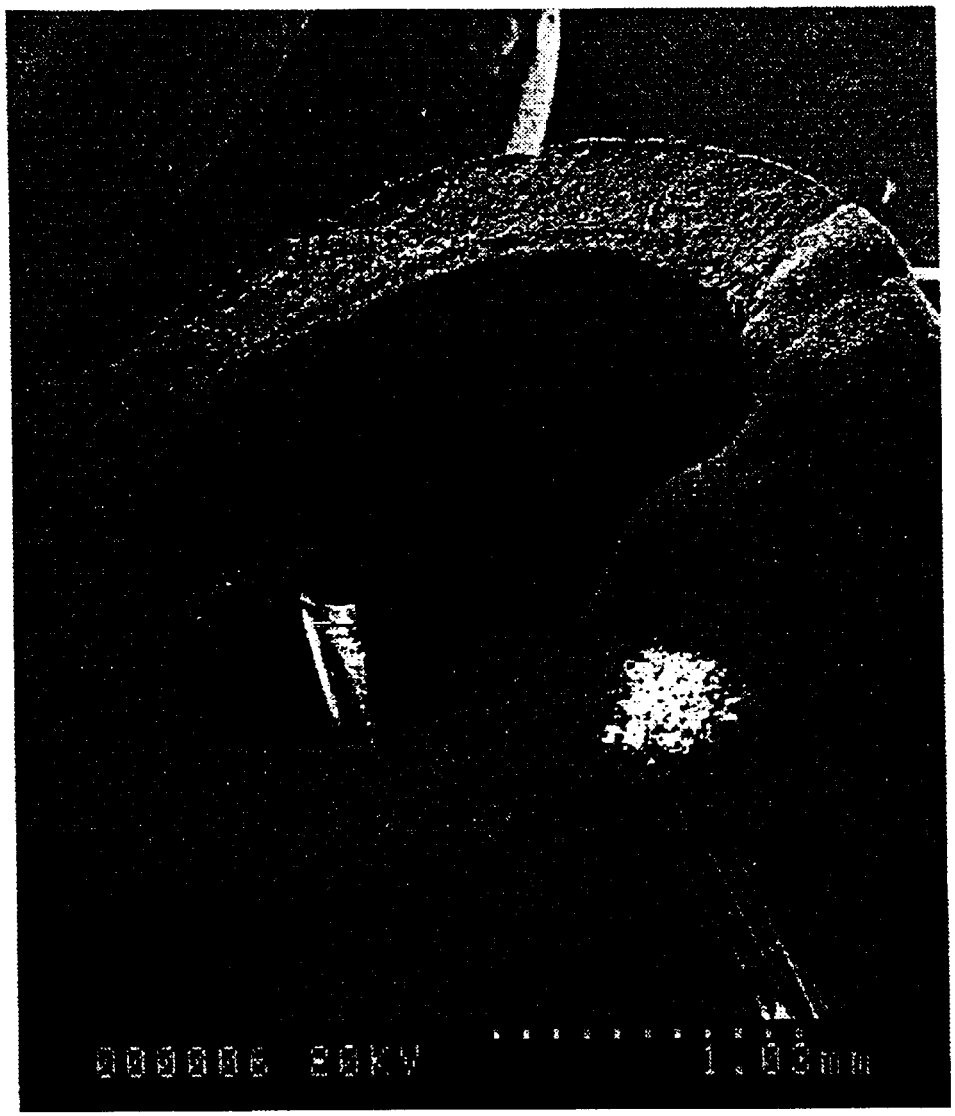
FIG. 23 shows a SEM micrograph of glass fibers situated in the outer lumen of the coatings with the mixture formulation of 2% glass fibers, 28.05% HEMA, 4.95% MMA, 67% water, 0.165% APS, 0.132% SMBS, 2500 rpm (also listed in Table 2 as Example 29) wherein the glass fibers were added to the monomer formulation.

A coating with particulates within the coating can be prepared with the same methodology as Example 1, except a particulate material with non-spherical shapes was included within the homogeneous monomer mixture. Glass fibers with an average diameter of 50 microns and between 1 and 10 cm in length were were added to the filtered monomer mixture as described in Table 2. Filtering the solution was not done after the fibers were added. Upon rotation of the mold, the dense particulates move to the inner surface of the mold. When the dense polymeric phase is gelled within the mold, a coating is formed that is shown in FIG. 23 removed from the mold. Such particulate-containing coatings can be made using any material for the tube that is conducive to this manufacturing process, and particulates that are fibers included, but are not limited to; glass, carbon nanofibers, biodegradable polymeric fibers, such as polyesters, poly carbonates, polydioxanone, poly (hydroxybutyrate, polylactide, polyglycolide, copolymers of lactide and glycolide that is compatible with the formulation mixture.

EXAMPLE 30

Morphology of a cross-section of the wall of a multi-layered tube with particulates situated near the inner lumen of the coating the mixture formulation listed in Table 2 as example 30. These multi-layered, particulate tubes are can be manufactured with the same methodology as Example 1, repeated as many times as required. Example 30 in Table 2 refers to the first, outer, layer formed (o) and the second, inner formed layer which contains particulates (i). Multi-layered hollow structures are possible by forming one layer and using the formed hollow structure as the surface coating of the mold and the hollow structure process repeated as many times as desired, with particulates included at any stage of the process. Following the first polymerization, the coating is not removed from the glass mold but instead the remaining mixture is drained, the mold is resealed, and a new formulation containing HEMA monomer, cross-linker, initiator, and microspheres, is injected into the mold containing the tube. The mold is inserted into a drill chuck and spun for a second time. The multi-layered hollow structures can be manufactured using any or all of the types of tubes described in the examples, made from any material, similar or different materials, in any order required, containing particluates in any or all layers, as many times as required. An example is shown in FIG. 24. The gel-like coating on the inner surface of the mold contains polycaprolactone microspheres embedded on the outer portion of the inner coating. FIG. 24 shows a scanning electron microscope (SEM) micrograph of a coating containing poly(caprolactone) microspheres, in which microspheres are distributed uniformly along the length of the coating, however a coating with non-uniformly distributed along the length can be created using methodology outlined in Example 27.

EXAMPLE 31

Figure 25:
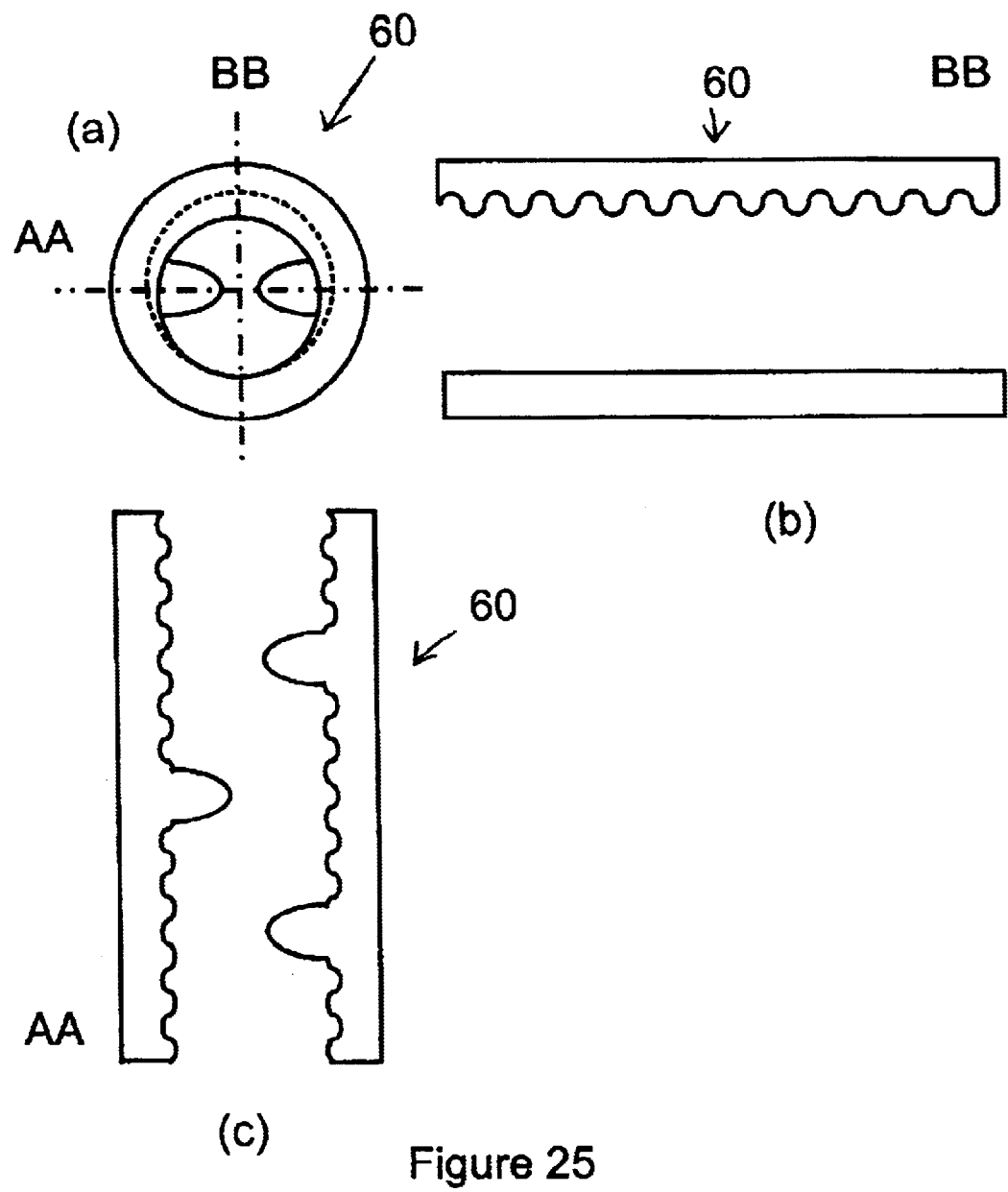
FIG. 25(a) is an end view of an alternative embodiment of a mold having a non-symmetrical cross section.
FIG. 25(b) is a cross section taken along the line BB of the mold of FIG. 25(a)
FIG. 25(c) is a cross section taken along the line AA of the mold of FIG. 25(a)

Various shaped structures can be manufactured with the same methodology as Example 1, except the mold shape is non-symmetrical along any axis. FIG. 25 is an example of such a mold that results in a hollow structure that is corrigated on one side, and smooth on the other, and contains spherical dimples along the length of the structure. Any example formulation can be used to create this shape of hollow structure, in a mold with a variable diameter.

EXAMPLE 32

Figure 26:
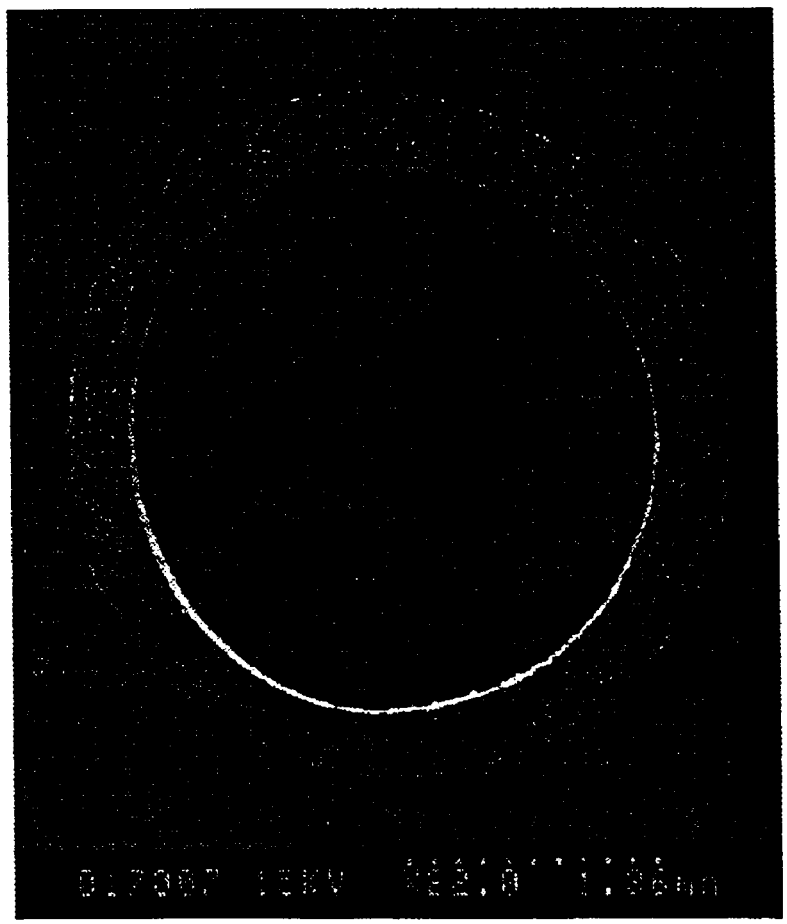
FIG. 26 shows a SEM micrograph of the lateral cross-section of a tube produced with the mixture formulation of 25% HEMA, 72.5% water, 2.5% MMA, 0.1% APS, 0.075% SMBS, 4000 rpm (also listed in Table 2 as Example 32), with the monomer solution permitted to phase separate before introduction into the mold.

A coating with both gel-like and porous morphologies was prepared with the same methodology as Example 1, except the initiated monomer mixture was allowed to phase separate before it was injected into the molds. The monomer mixture was permitted to phase separate inside the injecting device, and the heterogeneous solution was injected into the molds. The sealed mold was then placed in the chuck of a drill as prevously described in Example 1. The monomer mixture and rotation conditions used in Example 32 are listed in Table 2. The resulting porous material/gel-like coating after removal from the mold is shown in FIGS. 26a and 26b.

EXAMPLE 33

Figure 27:
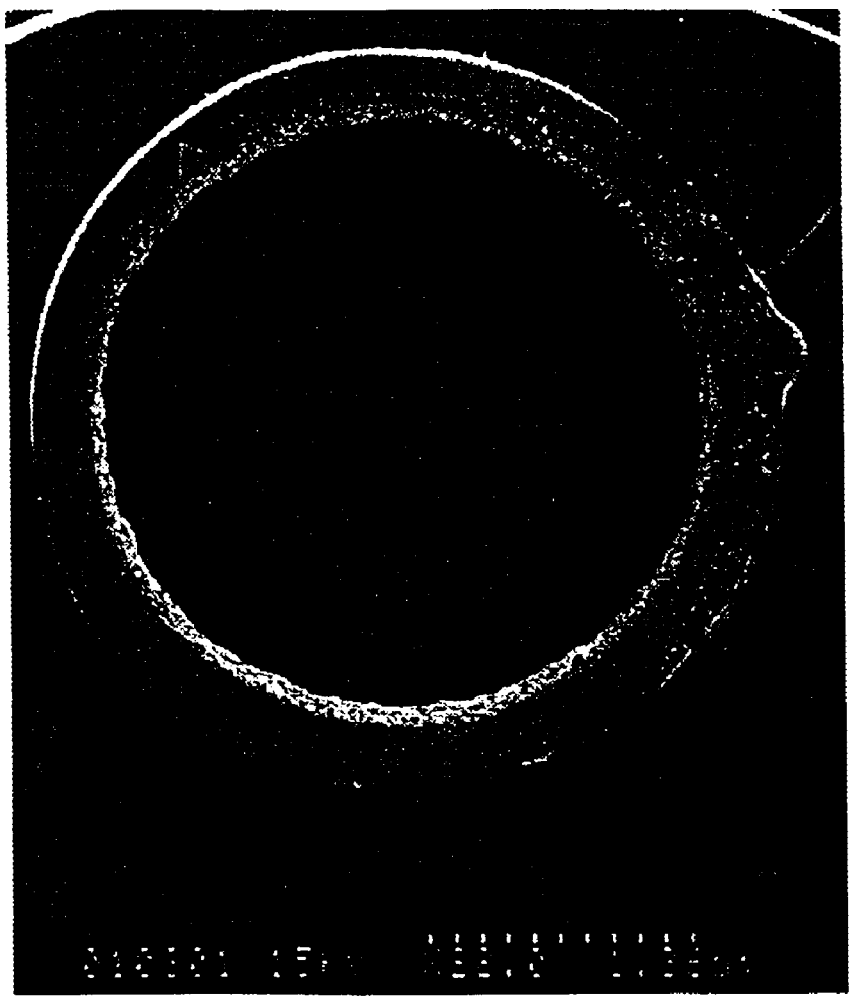
FIG. 27 shows a SEM micrograph of the lateral cross-section of a tube produced with the mixture formulation of 21.3% HEMA, 74.4% water, 2.1% MMA, 0.12% APS, 0.1% SMBS, 4000 rpm (also listed in Table 2 as Example 33), with the monomer solution permitted to phase separate inside the mold, but before rotation.

A coating with both gel-like and porous morphologies was prepared with the same methodology as Example 1, except the initiated monomer mixture was allowed to phase separate while it was in the molds, before rotation. The monomer mixture and rotation conditions used in Example 33 are listed in Table 2. The resulting porous material/gel-like hybrid coating on the inner surface of the mold is shown in FIG. 27.

EXAMPLES 34 & 35

A coating with both gel-like and porous morphologies was prepared with the same methodology as Example 1, except the mold contains an object predominantly made of wires. The coating that can be either gel-like or have porous morphology or both was prepared with similar methodology as in Example 1. Prior to the injection of a mixture into the mold, an object predominantly made of wires is inserted into the mold (FIGS. 28 & 29). Example 34 is a metallic stent that is placed inside a mold with the same inner diameter as the outer diameter of the stent. After insertion of the stent into the mold, the homogeneous mixture listed in Table 2 as Example 34 is injected into the mold and the mold rotated at the speed listed in Table 2. The resulting coated stent is shown in FIG. 28. Example 35 is a coiled wire that was shaped by winding the wire around a metallic rod. After insertion of the coiled wire into the mold, the homogeneous mixture listed in Table 2 as Example 34 is injected into the mold and the mold rotated at the speed listed in Table 2. The resulting coating containing the manganese coiled wire is removed from the mold and is shown in FIG. 29. The coiled wire or stent could be composed of polymer, metal or ceramic material.

EXAMPLES 36–37

A mixed porous/gel-like tube with radial porosity can be manufactured with the same methodology as Example 1, with the ratio of porous to gel-like component varied by the surface chemistry of the polymerization mold. FIG. 30 shows three coatings, removed from the mold, that were fabricated with a) clean glass mold, b) glass mold modified with 2-Methoxy(polyethyleneoxy) propyl trimethoxysilane (MPEOS—Example 36) and c) glass mold modified with N-(2-aminoethyl)-3-aminopropyl trimethoxysilane (AEAPS—Example 37). The glass molds were sonicated for 10 minutes in Glass & Plastic Cleaner™ 100 solution, rinsed with deionized water, and air dried for 30 minutes. The monomer mixture and rotation conditions used in Examples 36 and 37 are listed in Table 2. The resulting porous material/gel-like hybrid coating removed from the mold is shown in FIG. 30a. For surface modification of the glass mold with both MPEOS and AEAPS, the cleaned glass was activated by dipping for 10 min in a solution of 9:1 v/v conc $H_2SO_4/H_2O_2$, and the rinsed with plenty of water and air dried for 30 min. For Example 36, the glass molds were immersed in a 2 wt % MPEOS solution in water:methanol (5:95 wt %) solution with a pH of 2 only, adjusted by adding concentrated HCl. The surface modification reaction took place for 15 min at 40° C. The reaction was completed by drying the silane-treated glass in air for 30 min at 110° C. The resulting porous material/gel-like hybrid coating removed from the mold is shown in FIG. 30b with considerably higher proportion of gel within the coating wall than the coating in FIG. 30a.

For Example 37, surface modification of the glass molds with AEAPS was achieved by immersion in a 2 wt % AEAPS solution in water:methanol (5:95 wt %) solution for 15 min at 40° C. The reaction was completed by drying the silane-treated glass in air for 30 min at 110° C. The resulting porous material/gel-like hybrid coating removed from the mold is shown in FIG. 30c with considerably higher proportion of porous material within the coating wall than the coating in FIG. 30a. The coating shown in the SEM micrograph in FIGS. 30b and 30c was synthesized with the same formulation as FIG. 30a, but was formed in surface-modified molds.

EXAMPLE 38

Figure 31:
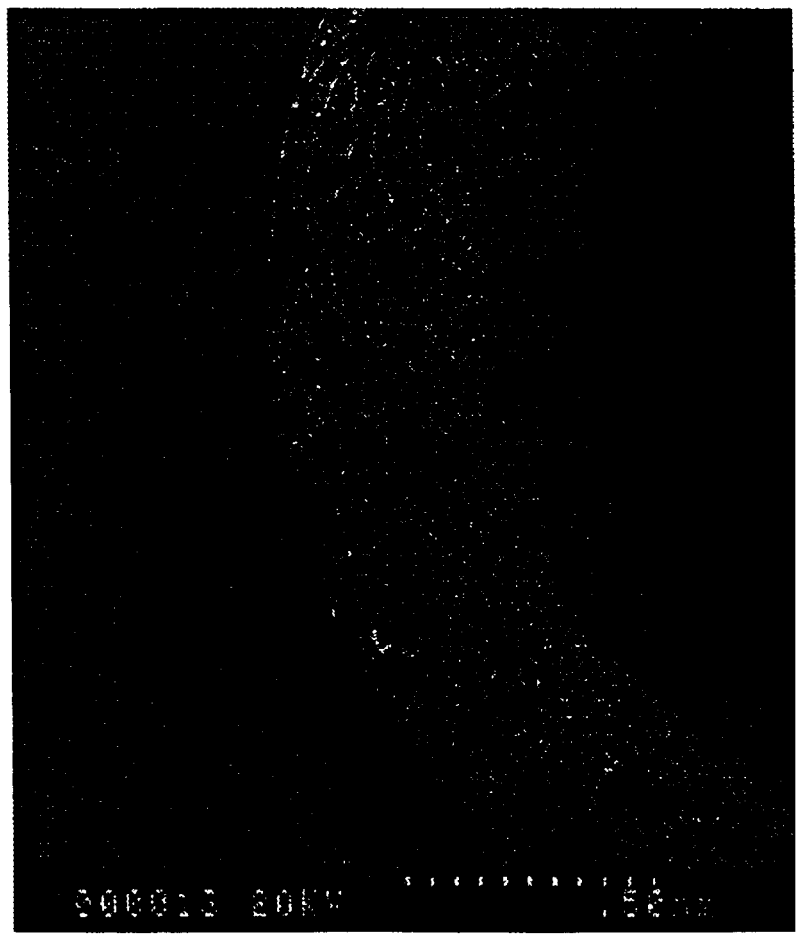
FIG. 31 shows an SEM micrograph of a cross-section of the wall of a mixed porous/gel-like tube produced with the mixture formulation of 10% dex-GMA, 40,000 g/mol, degree of substitution 10%, 10% PEG, 10 000 g/mol, 80% water, 0.14% APS, 0.018% SMBS, 6000 rpm (also listed in Table 1 as Example 38)

A mixed porous/gel-like coating with either non-degradable or degradable properties can be manufactured with the same methodology as Example 1, except the two phases always exist and are and insoluble in each other. Glycidyl methacrylated derivatized dextrans (dex-GMA) with varying degree of substitution (DS, the number of methacrylate groups per 100 glucopyranose residues) were synthesized by anchoring glycidyl methacrylate to dextran, with molecular weight as described in Table 2 for Example 38, in dimethylsulfoxide (DMSO) using N,N-dimethylaminopyridine (DMAP) as a catalyst, as adapted from the experimental methodology proposed Van Dijk-Wolthuis et al. (Macromolecules 28, (1995) 6317–6322). Polyethylene glycol (PEG, Mw of 10,000 g/mol) was dissolved in 0.22 M KCl to a concentration of 0.2 g/ml–0.4 g/ml. Dex-GMA was dissolved in 0.22 M KCl to a concentration of 0.2 g/ml–0.4 g/ml. Both solutions and an additional volume of 0.22 M KCl solution were filtered using syringe prefilters and then degassed for 10 minutes. Different volumes of each solution were mixed together to final composition as listed in Table 2 for Example 38. The mixture was vortexed for 2 minutes resulting in a water-in-water emulsion. Dex-GMA was polymerized preferably using, but not limited to a free radical initiating system and preferably an ammonium persulfate (APS)/sodium metabisulfite (SMBS) redox initiating system. Short vortexing of the solution was repeated after the appropriate amount of 0.1 g/ml APS solution, listed in Table 2 for Example 38, was added. The appropriate volume of 0.015 g/ml SMBS solution, listed in Table 2 for Example 38, was added to this mixture, which was briefly vortexed again. The mixture was then injected into a glass mold as described for Example 1. The mold was placed in the chuck of a drill that had been mounted horizontally, using a spirit level. The rotational speed was 6000 rpm as listed in Table 2 for Example 38. A SEM micrograph of the resulting degradable or non-degradable coating is shown in FIG. 31, with gel-like morphology on the outer portion of the wall, and porous morphology on the inner portion of the wall.

EXAMPLE 39

Figure 32:
FIG. 32 shows an SEM micrograph of a cross-section of the wall of a mixed porous/gel-like tube produced with the mixture formulation of 10% dex-GMA, 40,000 g/mol, degree of substitution 10%, 20% PEG, 10 000 g/mol, 70% water, 0.14% APS, 0.018% SMBS, 6000 rpm (also listed in Table 1 as Example 39)

A mixed porous/gel-like coating with either non-degradable or degradable properties and unique channels in the gel-like phase can be manufactured with the same methodology as Example 38, except the ratio of PEG to water is increased. Different volumes of each solution were mixed together to final composition as listed in Table 2 for Example 39. A SEM micrograph of the resulting degradable or non-degradable coating is shown in FIG. 32.

EXAMPLE 40

Figure 33:
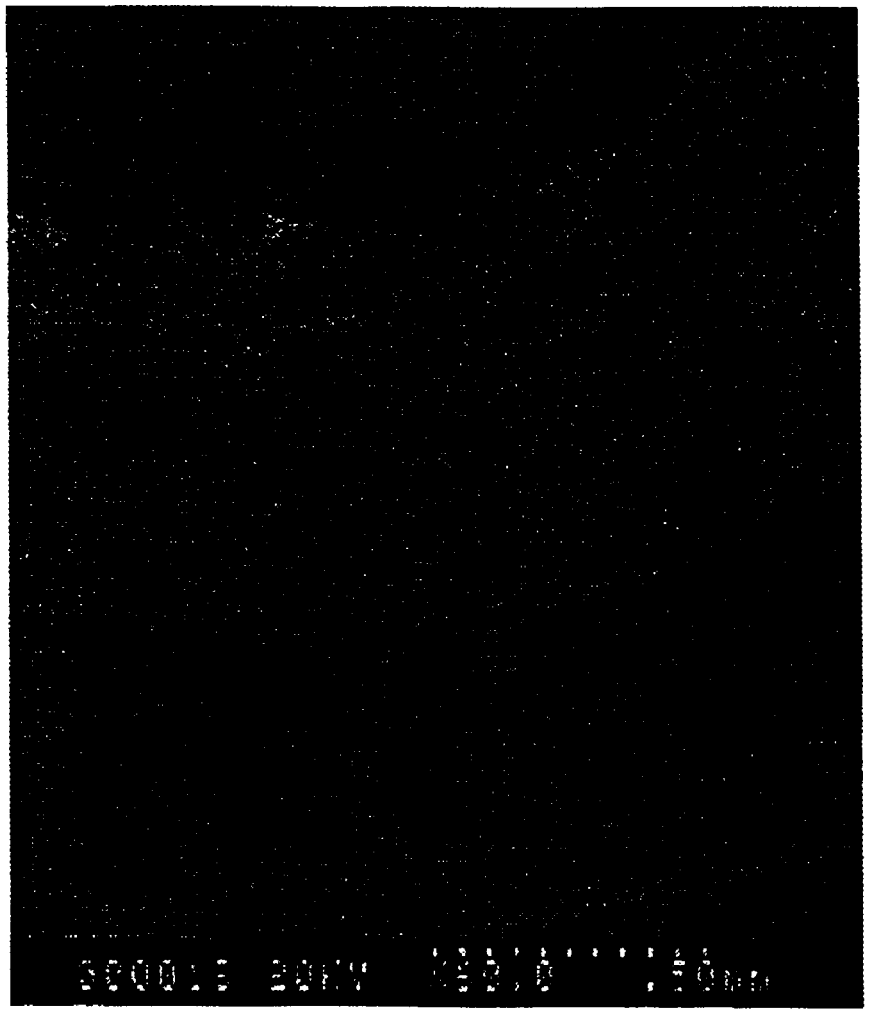
FIG. 33 shows an SEM micrograph of a cross-section of the wall of a mixed porous/gel-like tube produced with the mixture formulation of 20% dex-GMA, 40,000 g/mol, degree of substitution 10%, 10% PEG, 10 000 g/mol, 70% water, 0.28% APS, 0.035% SMBS, 6000 rpm (also listed in Table 1 as Example 40)

A mixed porous/gel-like coating with either non-degradable or degradable properties and sharp, defined separation of two wall morphologies shown in FIG. 33 can be manufactured with the same methodology as Example 38, except the percentage of dex-GMA in the composition was increased. Different volumes of each solution were mixed together to final composition as listed in Table 2 for Example 40. A SEM micrograph of the resulting degradable or non-degradable coating is shown in FIG. 33.

EXAMPLE 41

A mixed porous/gel-like coating with either non-degradable or degradable properties can be manufactured with the same methodology as Example 40, except the percentage of PEG in the composition was increased and the percentage of water in the composition decreased. Different volumes of each solution were mixed together to final composition as listed in Table 2 for Example 41.

EXAMPLE 42

Figure 34:
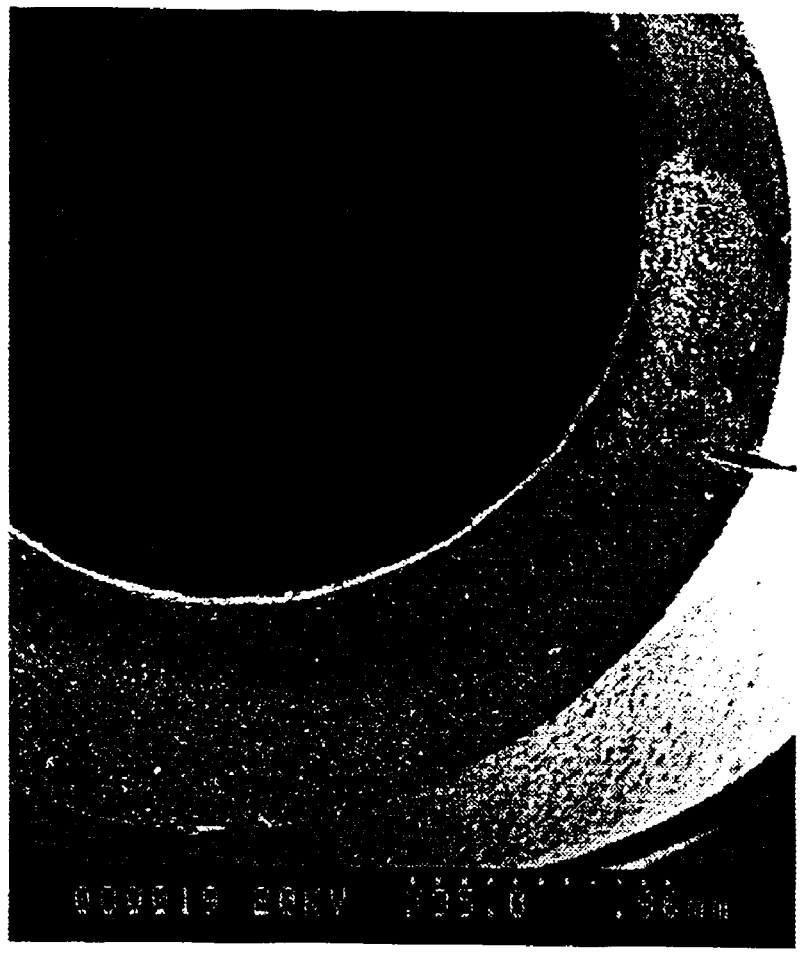
FIG. 34 shows an SEM micrograph of a cross-section of the wall of a mixed porous/gel-like tube produced with the mixture formulation of 20% dex-GMA, 6,000 g/mol, degree of substitution 10%, 10% PEG, 10 000 g/mol, 70% water, 0.28% APS, 0.035% SMBS, 6000 rpm (also listed in Table 1 as Example 42)

A predominantly gel-like coating with either non-degradable or degradable properties can be manufactured with the same methodology as Example 40, except the molecular weight of dex-GMA used in the composition was significantly lower as listed in Table 2. Different volumes of each solution were mixed together to final composition as listed in Table 2 for Example 42. A SEM micrograph of the resulting degradable or non-degradable coating is shown in FIG. 34 and reveals the compactness of the wall.

EXAMPLE 43

A mixed porous/gel-like coating with either non-degradable or degradable properties can be manufactured with the same methodology as Example 42, except the percentage of PEG in the composition was increased and the percentage of water in the composition decreased. Different volumes of each solution were mixed together to final composition as listed in Table 2 for Example 43.

EXAMPLE 44

Figure 35:
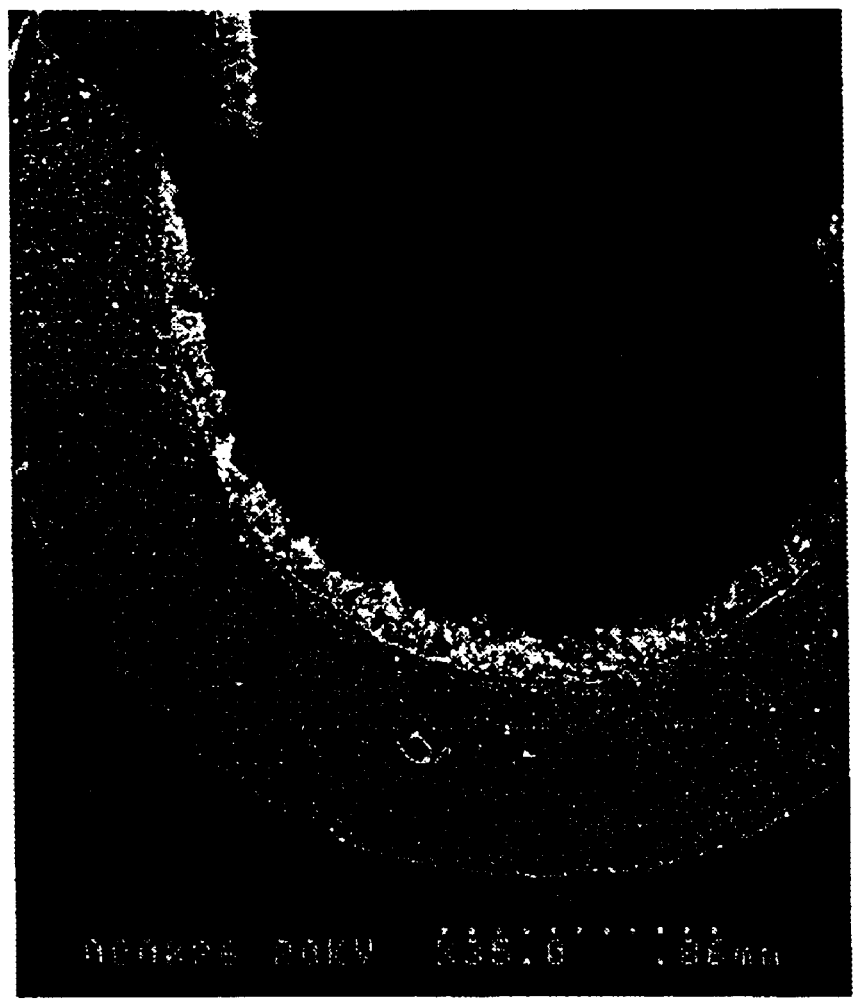
FIG. 35 shows an SEM micrograph of a cross-section of the wall of a mixed porous/gel-like tube produced with the mixture formulation of 30% dex-GMA, 6,000 g/mol, degree of substitution 10%, 10% PEG, 10 000 g/mol, 60% water, 0.42% APS, 0.053% SMBS, 6000 rpm (also listed in Table 1 as Example 44).

A predominantly gel-like coating with either non-degradable or degradable properties and a porous inner lumen can be manufactured with the same methodology as Example 42, except the percentage of dex-GMA in the composition was increased and the percentage of water in the composition decreased as listed in Table 2. Different volumes of each solution were mixed together to final composition as listed in Table 2 for Example 44. FIG. 35 shows the compactness of the wall morphology and porous inner lumen for Example 44.

EXAMPLE 45

A mixed porous/gel-like coating with degradable properties can be manufactured with the same methodology as Example 37, except the polymerizing polymer is 2-hydroxyethyl methacrylate-derivatized dextrans (dex-HEMA). Different volumes of each solution were mixed together to final composition as listed in Table 2 for Example 45.

EXAMPLE 46

A mixed porous/gel-like coating with degradable properties can be manufactured with the same methodology as Example 45, except the percentage of dex-HEMA in the composition was increased, the percentage of water in the composition decreased. Different volumes of each solution were mixed together to final composition as listed in Table 2 for Example 46.

EXAMPLE 47

A mixed porous/gel-like coating with with either non-degradable or degradable properties can be manufactured with the same methodology as Example 38, except Pluronic F68 replaced PEG to a final composition as listed in Table 2 for Example 47.

EXAMPLE 48

A mixed porous/gel-like coating containing microspheres can be manufactured with the same methodology as Example 38, except an enzyme degrading particulate was included in the mixture which degrades the polymer backbone. Different quantities of dex-GMA, PEG, dextranase containing PCL microspheres and water solution were mixed together to a final composition as listed in Table 2 for Example 48. The mixed porous/gel-like coating is non-degradable by hydrolysis, but is susceptible to degradation in the presence of enzymes. The PCL microspheres incorporated in the wall of the coating degrade with hydrolysis and release the enzyme, which degrades the coating by scission of the polymer backbone.

EXAMPLE 49

A mixed porous/gel-like coating with degradable properties can be manufactured with the same methodology as Example 38, except the polymerizing polymer is dex-oligopeptide-methacrylate. Different quantities of dex-Lys-Pro-Leu-Gly-Ile-Ala-methacrylate, PEG, and water solution were mixed together to a final composition as listed in Table 2 for Example 49. The mixed porous/gel-like coating is non-degradable by hydrolysis, but is susceptible to degradation in the presence of cell-secreted enzyme, gelatinase A (MMP2), which degrades the coating by scission of the oligopeptide crosslink.

EXAMPLE 50

A mixed porous/gel-like coating containing microspheres can be manufactured with the same methodology as Example 49, except an enzyme degrading particulate was included in the mixture which degrades the crosslinking agent.

Different quantities of dex-Lys-Pro-Leu-Gly-Ile-Ala-methacrylate, PEG, MMP2 containing PCL microspheres and water solution were mixed together to a final composition as listed in Table 2 for Example 50. The mixed porous/gel-like coating is non-degradable by hydrolysis, but is susceptible to degradation in the presence of MMP2. The PCL microspheres incorporated in the wall of the coating degrade with hydrolysis and release the enzyme, which degrades the coating by scission of the oligopeptide crosslink.

EXAMPLE 51

A mixed porous/gel-like coating with degradable properties can be manufactured with the same methodology as Example 38, except an enzyme, which was entrapped in the coating during polymerization, was included in the mixture, which degrades the polymer backbone. Different quantities of dex-GMA, PEG, dextranase and water solution were mixed together to a final composition as listed in Table 2 for Example 48. The mixed porous/gel-like coating is non-degradable by hydrolysis, but is susceptible to degradation of the polymer backbone in the presence of enzymes.

As used herein, the terms "comprises", "comprising", "including" and "includes" are to be construed as being inclusive and open ended, and not exclusive. Specifically, when used in this specification including claims, the terms "comprises", "comprising", "including" and "includes" and variations thereof mean the specified features, steps or components are included. These terms are not to be interpreted to exclude the presence of other features, steps or components.

The foregoing description of the preferred embodiments of the invention has been presented to illustrate the principles of the invention and not to limit the invention to the particular embodiment illustrated. It is intended that the scope of the invention be defined by all of the embodiments encompassed within the following claims and their equivalents.

TABLE 1

Example Formulations

| Example # | Monomer 1 | Monomer 2 | Monomer 3 | Solvent 1 | Solvent 2 | Initiator 1 | Accelerator | Rotation | Tube ID |
|---|---|---|---|---|---|---|---|---|---|
| 1 | 1% HEMA | | | 99% water | | 0.01% APS | 0.01% SMBS | 4000 rpm | 2.4 mm |
| 2 | 1.9% HEMA | 0.1% PEGMA | | 98% water | | 0.02% APS | 0.02% SMBS | 2700 rpm | 3.2 mm |
| 3 | 7% HEMA | | | 93% water | | 0.05% APS | 0.04% SMBS | 4000 rpm | 7.5 mm |
| 4 | 15.75% HEMA | 2.25% MMA | 0.02% EDMA | 82% water | | 0.08% APS | 0.06% SMBS | 2700 rpm | 3.2 mm |
| 5 | 20% HEMA | 0.06% EDMA | | 80% water | | 0.1% APS | 0.04% TEMED | 2700 rpm | 2.4 mm |
| 6 | 20% HEMA | | 0.02% EDMA | 80% water | | 0.1% APS | 0.06% SMBS | 10000 rpm | 2.4 mm |
| 7 | 23.25% HEMA | 1.75% MMA | | 75% water | | 0.125% APS | 0.1% SMBS | 2500 rpm | 3.2 mm |
| 8 | 28.3% HEMA | 5.3% MMA | | 58.3% water | 8.3% EG | 0.125% APS | 0.1% SMBS | 2700 rpm | 1.8 mm |
| 9 | 27% HEMA | 3% MMA | | 70% water | | 0.1 APS | 0.075% SMBS | 4000 rpm | 2.4 mm |
| 10 | 27% HEMA | 3% MMA | | 70% water | | 0.15% APS | 0.12% SMBS | 2700 rpm | 2.4 mm |
| 11 | 20% HEMA | | | 80% water | | 0.1% APS | 0.4% SMBS | 2700 rpm | 3.2 mm |
| 12 | 2% HEMA | | | 98% water | | 0.02% APS | 0.02% SMBS | 30 rpm | 3.2 mm |
| 13(o) | 1.8% HEMA | 0.2% PEGMA | | 98% water | | 0.002% APS | 0.002% SMBS | 2700 rpm | 3.2 mm |
| 13 (i) | 27% HEMA | | 3% MMA | 70% water | | 0.12% APS | 0.09% SMBS | 4000 rpm | |
| 14 | 20% HEMA | | 0.02% EDMA | 80% water | | 0.1% APS | 0.04% SMBS | 2700 rpm | 2.4 mm |
| 15 | 28.3% HEMA | 5.3% MMA | | 58.3% water | 8.3% EG | 0.15% APS | 0.12% SMBS | 2700 rpm | 1.8 mm |
| 16 | 27.3% HEMA | 2.7% MMA | 0.03% EDMA | 70% water | | 0.12% APS | 0.09% SMBS | 4000 rpm | 3.2 mm |
| 17 | 22.5% HEMA | 2.5% MMA | | 75% water | | 0.125% APS | 0.1% SMBS | 4000 rpm | 0.45 mm |
| 18 | 23.25% HEMA | 1.75% MMA | | 75% water | | 0.125% APS | 0.1% SMBS | 2500 rpm | 2.8 mm to 5.8 mm |
| 22 | 30 vol % HPMA | 1% MBAm | | 65% acetone | 4.9% DMSO | 1% AIBN | | 4000 rpm | 3.2 mm |

TABLE 2

Example Formulations

| Example # | Monomer 1 | Monomer 2 | Monomer 3 | particulate | Solvent 1 | Solvent 2 | Initiator | accelerator | Rotation | Tube ID |
|---|---|---|---|---|---|---|---|---|---|---|
| 25 | 19.77% HEMA | | 0.02% EDMA | 1% PCL microspheres | 79.04% $H_2O$ | | 0.1% APS | 0.04% SMBS | 2700 rpm | 2.4 mm |
| 27 | 19.77% HEMA | | 0.02% EDMA | 1% PCL microspheres | 79.04% $H_2O$ | | 0.1% APS | 0.04% SMBS | 2700 rpm | 2.4 mm |
| 28 | 2% HEMA | — | 0.002% EDMA | 1% PCL microspheres with NGF & OVA | 98% $H_2O$ | | 0.1% APS | 0.04% SMBS | 6000 rpm | |
| 29 | 28.05% HEMA | 4.95% MMA | | 2% Glass fibers | 67% $H_2O$ | | 0.165% APS | 0.132% SMBS | 2500 rpm | 2.4 mm |
| 30 (o) | 23% HEMA | 2% MMA | 0.002% EDMA | | 75% $H_2O$ | | 0.125% APS | 0.1% SMBS | 6000 rpm | 4.2 mm |
| 30 (i) | 2% HEMA | | 0.02% EDMA | 1% PCL microspheres with NGF & OVA | 98% $H_2O$ | | 0.1% APS | 0.04% SMBS | 6000 rpm | |
| 32 | 25% HEMA | 2.5% MMA | | | 72.5% $H_2O$ | | 0.1% APS | 0.075% SMBS | 4000 rpm | 4.2 mm |
| 33 | 21.3% HEMA | 2.1% MMA | | | 74.4% $H_2O$ | | 0.12% APS | 0.1% SMBS | 4000 rpm | 4.2 mm |
| 34 | 22.5% HEMA | 2.5% MMA | | stent | 75% $H_2O$ | | 0.2% APS | 0.15% SMBS | 6000 rpm | 2.2 mm |
| 35 | 28.05% HEMA | 4.95% MMA | | Coiled Mn wire | 67% $H_2O$ | | 0.165% APS | 0.132% SMBS | 2500 rpm | 2.4 mm |
| 36 | 28.05% HEMA | 4.95% MMA | | | 67% $H_2O$ | | 0.165% APS | 0.132% SMBS | 2500 rpm | 2.4 mm |
| 37 | 28.05% HEMA | 4.95% MMA | | | 67% $H_2O$ | | 0.165% APS | 0.132% SMBS | 2500 rpm | 2.4 mm |
| 38 | 10% Dex-GMA, 40 K MW, DS 10 | | | | 10% PEG 10 K g/mol | 80% $H_2O$ | 0.14% APS | 0.018% SMBS | 6000 rpm | 4.6 mm |
| 39 | 10% Dex-GMA, 40 K MW, DS 10 | | | | 20% PEG 10 K g/mol | 70% $H_2O$ | 0.14% APS | 0.018% SMBS | 6000 rpm | 4.8 mm |
| 40 | 20% Dex-GMA, 40 K MW, DS 10 | | | | 10% PEG 10 K g/mol | 70% $H_2O$ | 0.28% APS | 0.035% SMBS | 6000 rpm | 4.8 mm |

TABLE 2-continued

Example Formulations

| Example # | Monomer 1 | Monomer 2 | Monomer 3 | particulate | Solvent 1 | Solvent 2 | Initiator | accelerator | Rotation | Tube ID |
|---|---|---|---|---|---|---|---|---|---|---|
| 41 | 20% Dex-GMA, 40 K MW, DS 10 | | | | 20% PEG 10 K g/mol | 60% $H_2O$ | 0.28% APS | 0.035% SMBS | 6000 rpm | 4.8 mm |
| 42 | 20% Dex-GMA, 6 K MW, DS 10 | | | | 10% PEG 10 K g/mol | 70% $H_2O$ | 0.28% APS | 0.035% SMBS | 6000 rpm | 4.8 mm |
| 43 | 20% Dex-GMA, 6 K MW, DS 10 | | | | 20% PEG 10 K g/mol | 60% $H_2O$ | 0.28% APS | 0.035% SMBS | 6000 rpm | 4.3 mm |
| 44 | 30% Dex-GMA, 6 K MW, DS 10 | | | | 10% PEG 10 K g/mol | 60% $H_2O$ | 0.42% APS | 0.053% SMBS | 6000 rpm | 4.5 mm |
| 45 | 10% Dex-HEMA, 40 K MW, DS 10 | | | | 10% PEG 10 K g/mol | 80% $H_2O$ | 0.14% APS | 0.018% SMBS | 6000 rpm | 4.3 mm |
| 46 | 20% Dex-HEMA, 40 K MW, DS 10 | | | | 20% PEG 10 K g/mol | 60% $H_2O$ | 0.28% APS | 0.035% SMBS | 6000 rpm | 4.8 mm |
| 47 | 10% Dex-GMA, 40 K MW, DS 10 | | | | 10% Pluronic F68 | 80% $H_2O$ | 0.14% APS | 0.018% SMBS | 6000 rpm | 4.6 mm |
| 48 | 10% Dex-GMA, 40 K MW, DS 10 | | | 1% PCL microspheres with dextranase & OVA | 10% PEG 10 K g/mol | 80% $H_2O$ | 0.14% APS | 0.018% SMBS | 6000 rpm | 4.6 mm |
| 49 | 10% Dex-Lys-Pro-Leu-Gly-Ile-Ala-methcrylate, 40 K MW, DS 10 | | | | 10% PEG 10 K g/mol | 80% $H_2O$ | 0.14% APS | 0.018% SMBS | 6000 rpm | 4.6 mm |
| 50 | 10% Dex-Lys-Pro-Leu-Gly-Ile-Ala-methacrylate, 40 K MW, DS 10 | | | 1% PCL microspheres with MMP2 & OVA | 10% PEG 10 K g/mol | 80% $H_2O$ | 0.14% APS | 0.018% SMBS | 6000 rpm | 4.6 mm |
| 51 | 10% Dex-GMA, 40 K MW, DS 10 | | | 2 Units/g dextranase | 10% PEG 10 K g/mol | 80% $H_2O$ | 0.14% APS | 0.018% SMBS | 6000 rpm | 4.6 mm |

Therefore what is claimed is:

1. A process of producing a product, comprising:
   a) filling an interior of a mold with a mixture so that substantially all gas bubbles are displaced therefrom, the mixture comprising at least two components which can be phase separated by a phase separation agent into at least two phases;
   b) rotating said mold said mixture at an effective rotational velocity in the presence of said phase separation agent so that under rotation at least one of the phases deposits onto an inner surface of the mold; and
   c) forming said product by stabilizing said at least one of the phases deposited onto the inner surface of the mold.

2. The process according to claim 1 including removing said product from said mold.

3. The process according to claim 2 wherein of said at least two components, at least one is selected from the group consisting of the group of monomers and macromers and the other is at least one solvent, wherein said at least one of the phases that deposits onto the inner surface includes at least the monomer or macromer, and wherein the step of stabilizing said deposited phase includes gelation of the monomer or macromer by polymerization thereof.

4. The process according to claim 3 wherein said phase separation agent is selected from the group consisting of solution immiscibility, light, pH, initiation agents, change in temperature, creation of a chemical product within the mold, changes in cationic and/or anionic concentrations, electric and magnetic fields.

5. The process according to claim 4 wherein said initiation agent is selected from the group consisting of free radical initiators, thermal and photo initiators, redox initiators, anionic, cationic or ring-opening initiators.

6. The process according to claim 1 wherein said at least two components includes at least one polymer dissolved in at least one solvent, and wherein said mixture is composed of at least two solutions, wherein said at least one of the phases that deposits on the inner surface includes at least the polymer, and wherein the step of stabilizing said deposited phase includes gelation thereof.

7. The process according to claim 6 wherein said phase separation agent is selected from the group consisting of solution immiscibility, light, change in pH, change in temperature, creation of a chemical product within the mold, changes in cationic and/or anionic concentrations, electric and magnetic fields.

8. The process according to claim 6 wherein gelation is achieved by exposure to an agent selected from the group consisting of light, change in pH, change in temperature, creation of a chemical product within the mold, changes in cationic and/or anionic concentrations, electric and magnetic fields.

9. The process according to claim 3 wherein said hollow mold is a cylindrical tube so that said product is a polymeric tube.

10. The process according to claim 9 wherein said cylindrical tube includes preselected surface features on said inner surface of the cylindrical tube.

11. The process according to claim 1 including inserting a porous structure into said mold prior to filling said mold with said mixture, and wherein said product is coated on an outer surface of said porous structure.

12. The process according to claim 3 wherein said mixture includes a cross-linking agent.

13. The process according to claims 12 wherein the crosslinking agent is selected from the group consisting of multifunctional ester, carbonate, multi-isocyanate, methacrylate, poly-N-isopropyl acrylamide, acrylate, acrylamide and methacrylamide.

14. The process according to claim 3 wherein said monomer is selected from the group consisting of acrylates, methacrylates, acrylic acid, methacrylic acid, acrylamides, methacrylamide, and derivatives thereof; N-vinyl pyrrolidone, acenaphthalene, N-vinyl acetamide, phenylacetylene, acrolein, methyl acrolein, N-vinyl pyridine, vinyl acetate, vinyl chloride, vinyl fluoride, vinyl methyl ketone, vinylidene chloride, styrene and derivatives thereof; propene, acrylonitrile, methacrylonitrile, acryloyl chloride, allyl acetate, allyl chloride, allylbenzene, butadiene and derivatives thereof; N-vinyl caprolactam, N-vinyl carbazole, cinnamates and derivatives thereof; citraconimide and derivatives thereof; crotonic acid, diallyl phthalate, ethylene and derivatives thereof; fumarates and derivatives thereof; hexene and derivatives thereof; isoprene and derivatives thereof; itaconate and derivatives thereof; itaconamide and derivatives thereof; diethyl maleate, 2-(acryloyloxy)ethyl diethyl phosphate, vinyl phosphonates and derivatives thereof; maleic anhydride, maleimide, silicone monomers, and derivatives thereof; lactones, lactams, carbonates, and any combination thereof.

15. The process according to claim 3 wherein said solvent is selected from the group consisting of a nucleophilic, electrophilic or amphiphilic molecules selected from the group consisting of water, alcohols, ethylene glycol, ethanol, acetone, poly(ethylene glycol) and derivatives thereof; solutions of poly(ethylene glycol), dimethyl sulfoxide, dimethyl formamide, alkanes and derivatives thereof; acetonitrile, acetic acid, benzene, acetic anhydride, benzyl acetate, carbon tetrachloride, chlorobenzene, n-butanol, 2-chloroethanol, chloroform, cyclohexane, cyclohexanol, dichloromethane, diethyl ether, di(ethylene glycol), di(ethylene glycol) monomethyl ether, 1,4-dioxane, N,N'-dimethyl acetamide, N,N'-dimethyl formamide, ethyl acetate, formaldehyde, n-heptane, hexachloroethane, hexane, isobutanol, isopropanol, methanol, methyl ethyl ketone, nitrobenzene, n-octane, n-pentanol, propyl acetate, propylene glycol, pyridine, tetrahydrofuran, toluene, trichloroethylene, o-xylene and p-xylene, a monomer, a macromer, a liquid crosslinking agent, or mixtures thereof.

16. The process according to claims 3 wherein said solvent solubilizes said monomer or macromer but not a polymer or crosslinked polymer formed from said monomer or macromer.

17. The process according to claims 3 wherein said at least one monomer or macromer is present in a range from about 0.001% by weight to about 75% by weight.

18. The process according to claims 3 wherein said at least one monomer or macromer is present in a range from about 0.001% by weight to about 60% by weight.

19. The process according to claim 6 wherein said polymer is selected from the group consisting of polyacrylates, polysulfones, peptide sequences, proteins and derivatives, oligopeptides, degradable polymer, collagen, gelatin, elastin, fibrin, fibronectin, laminin, polymethacrylates polyacetates, polyesters, polyamides, polycarbonates, polyanhydrides, polyamino acids carbohydrates, polysaccharides and modified polysaccharides, and derivatives.

20. The process according to claim 1 including physically or chemically modifying the inner surface of the mold upon which pre-selected morphologies are induced into the wall of the said product by inducing beading or spreading of the separated liquid phase.

21. The process according to claim 20 with molecules including silanating agents.

22. The process according to claim 3 including the step of removing the solvent and including repeating steps a), b) and c), at least once to produce a multi-layered product.

23. The process according to claim 3 including the step of removing the solvent and including repeating steps a), b) and c), and wherein said mixture includes particles in step a) to produce a multi-layered product with constituents embedded in the wall of the product, and wherein the constituents include one or a combination of cells, proteins, peptides, enzymes, genes, vectors, growth factors, hormones, nucleotides, therapeutics, drugs and carbohydrates.

24. The process according to claim 23 wherein said constituents are embedded directly in the wall of the product.

25. The process according to claim 23 wherein said constituents are embedded in microspheres or nanoparticles which are embedded in the wall of the product.

26. The process according to claim 6 including the step of removing the solvent and including repeating steps a), b) and c), and wherein said mixture includes particles in step a) to produce a multi-layered product with particles embedded in the wall of the product, and wherein the particles include one or a combination of cells, proteins, peptides, enzymes, genes, vectors, growth factors, hormones, nucleotides, therapeutics, drugs and carbohydrates.

27. The process according to claim 26 wherein said constituents are embedded directly in the wall of the product.

28. The process according to claim 26 wherein said constituents are embedded in microspheres or nanoparticles which are embedded in the wall of the product.

29. The process according to claim 1 wherein prior to filling up said mold with said mixture, said inner surface of said mold is treated in such a way so as to increase adherence of the product deposited thereon during rotation.

30. The process according to claim 1 wherein prior to filling up said mold with said mixture, said inner surface of said mold is treated in such a way so as to prevent adherence of the product deposited thereon during rotation.

31. The process according to claim 1 including a step of inserting an object into the mold to be coated with wherein said object is coated with said at least one of the phases which is stabilized on said object.

32. The process according to claim 1 wherein the object is selected from the group consisting of meshes, scaffolds, stents, coils, aural drainage tubes, abdominal/gastrointestinal structural replacements, stents for abdominal aortic aneurysms and esophageal scaffolds and fibers that occupy a periphery of the mold.

33. The process according to claim 1 wherein said mold is made of a material suitable to act as a nerve guidance channel and wherein said product is coated on the interior surface thereof.

34. The process according to claim 1 wherein said product is made of a material suitable to act as a nerve guidance channel.

35. The process according to claim 3 wherein said step c) by stabilizing said at least one of the phases deposited onto the inner surface of the mold is achieved by one or a combination of gelation, exposure of the phase to light, change in pH, change in temperature, creation of a chemical product within the mold, changes in cationic and/or anionic concentrations, electric and magnetic fields.

36. The process according to claim 6 wherein said step c) by stabilizing said at least one of the phases deposited onto the inner surface of the mold is achieved by one or a combination of gelation, exposure of the phase to light, change in pH, change in temperature, creation of a chemical product within the mold, changes in cationic and/or anionic concentrations, electric and magnetic fields.

37. The process according to claim 12 wherein the crosslinking agent is selected from the group consisting of ethylene glycol dimethacrylate(EDMA), hexamethylene dimethacrylate (HDMA), poly(ethylene glycol) dimethacrylate, 1,5-hexadiene-3,4-diol (DVG), 2,3-dihydroxybutanediol 1,4-dimethacrylate (BHDMA), 1,4-butanediol dimethacrylate (BDMA), 1,5-hexadiene (HD) multi-functional star polymers of poly(ethylene oxide), bifunctional peptides, oligopeptidic crosslinkers, proteins and protein fragments, including enzyme degradable crosslinking agents, hydrolysable crosslinking agent, oligopeptidic crosslinking agents, nitrenes and exposure to light.

38. The process according to claim 3 wherein said monomer is selected from the group consisting of 2-hydroxyethyl methacrylate, methyl methacrylate, 2-polyethylene glycol ethyl methacrylate, ethyl acrylate, 2-hydroxyethyl acrylate, 2-chloroethyl methacrylate, butyl methacrylate, glycidyl methacrylate, hydroxypropyl methacrylate, hydroxypropyl methacrylamide, N,N-diethyl acrylamide, N,N-dimethyl acrylamide, 2-chloroethyl acrylamide, 2-nitrobutyl acrylamide, 1,1 diphenyl-ethylene, chlorotrifluoro-ethylene, dichloroethylene, tetrachloro-ethylene isopropenyl acetate, isopropenyl methyl ketone, isopropenylisocyanate, and any combination thereof.

39. The process according to claim 6 wherein said polymer is selected from the group consisting of poly(methyl methacrylate), poly(ethoxyethyl methacrylate), poly(hydroxyethylmethacrylate); poly(vinyl acetate)s, poly(N-vinyl pyrrolidinone), poly(vinyl actetate), poly(vinyl alcohol), poly(hydroxypropyl methacrylamide), poly(caprolactone), poly(dioxanone) polyglycolic acid, polylactic acid, copolymers of lactic and glycolic acids, and poly(trimethylene carbonate)s, poly(butadiene), polystyrene, polyacrylonitrile, poly(chloroprene), neoprene, poly(isobutene), poly(isoprene), polypropylene, polytetrafluoroethylene, poly(vinylidene fluoride), poly(chlorotrifluoroethylene), poly(vinyl chloride), poly(oxymethylene), poly(ethylene terephthalate), poly(oxyethylene) poly(oxyterephthaloyl), poly[imino(1-oxohexamethylene)], poly(iminoadipoyl-iminohexamethalene), poly(iminohexamethylene-iminosebacoyl), poly[imino(1-oxododecamethylene)], cellulose, hyaluronic acid, sodium hyaluronate, alginate, dextran and modified dextran, agarose, chitosan and derivatives thereof; chitin, and mixtures thereof; starch and derivatives.

40. The process according to claim 6 wherein said polymer is selected from the group consisting of dextran-acrylates, dex-lactate-HEMA, dex-GMA and dex-HEMA.

* * * * *